United States Patent [19]
Cerami et al.

[11] Patent Number: 5,853,703
[45] Date of Patent: *Dec. 29, 1998

[54] PREVENTING AND REVERSING THE FORMATION OF ADVANCED GLYCOSYLATION ENDPRODUCTS

[75] Inventors: Anthony Cerami, Shelter Island, N.Y.; Peter C. Ulrich, Old Tappan, N.J.; Dilip R. Wagle, Valley Cottage, N.Y.; San-Bao Hwang, Sudbury, Mass.; Sara Vasan, Yonkers, N.Y.; John J. Egan, Mountain Lakes, N.J.

[73] Assignees: The Picower Institute for Medical Research, Manhasset, N.Y.; Alteon Inc., Ramsey, N.J.

[ * ] Notice: The term of this patent shall not extend beyond the expiration date of Pat. No. 5,656,261.

[21] Appl. No.: 588,249

[22] Filed: Jan. 18, 1996

Related U.S. Application Data

[63] Continuation-in-part of Ser. No. 473,104, Jun. 7, 1995, abandoned, which is a continuation-in-part of Ser. No. 375,155, Jan. 18, 1995, Pat. No. 5,656,261.

[51] Int. Cl.$^6$ .......................... A61K 31/38; C07D 277/24
[52] U.S. Cl. ................................ 424/53; 424/51; 424/52; 424/54; 424/56; 514/365; 514/367; 548/152; 548/161; 548/164; 548/179; 548/180; 548/190; 548/193; 548/194; 548/202; 548/203; 548/204; 548/205
[58] Field of Search ................................ 424/53, 51, 52, 424/54, 56; 514/365, 367; 548/512, 161, 164, 179, 180, 190, 193, 194, 202, 203, 204, 205

[56] References Cited

U.S. PATENT DOCUMENTS

| | | | |
|---|---|---|---|
| 4,609,670 | 9/1986 | Dominianni et al. | 435/7.1 |
| 4,683,312 | 7/1987 | Dominianni et al. | 435/7.1 |
| 4,758,583 | 7/1988 | Cerami et al. | 514/399 |
| 5,108,930 | 4/1992 | Ulrich et al. | 436/111 |
| 5,230,998 | 7/1993 | Neurath et al. | 435/7.1 |
| 5,262,152 | 11/1993 | Ulrich et al. | 436/111 |
| 5,366,885 | 11/1994 | Barranco, III | 435/6 |

FOREIGN PATENT DOCUMENTS

| | | |
|---|---|---|
| 167139 | 1/1986 | European Pat. Off. . |
| 170037 | 2/1986 | European Pat. Off. . |
| 364344 | 4/1990 | European Pat. Off. . |
| 586806 | 3/1994 | European Pat. Off. . |
| WO 94/11490 | 5/1994 | European Pat. Off. . |
| 614886 | 9/1994 | European Pat. Off. . |
| WO94/20083 | 9/1994 | European Pat. Off. . |
| 2323465 | 11/1973 | Germany . |
| 1143855 | 6/1989 | Japan . |
| 60-184038 | 4/1990 | Japan . |

OTHER PUBLICATIONS

Ulrich et al. (1985) Modern Aging Res. 7:83–92.
Pongor et al. (1984) Proc. Natl. Acad. Sci. USA 81:2684–8.
Kawakishi et al. (1994) Maillard React. Chem. Food Health. 151:281–5.
Tsuge et al. (1982) Chem. Lett. 5:711–4.
Archer et al. (1979) J. Med. Chem. 22:306–9.
Singh et al. (1992) Tetrahedron 48:4545–50.
Gandasegui et al. (1990) Heterocycles 31:1801–9.
Makita et al. (1992) J. Biol. Chem. 267:5133–8.
Chang et al. (1985) J. Biol. Chem. 260:7970–4.
Voller et al. (1985) Enzyme Immunoassays, Alternative Immunoassays, pp. 77–86.
Brownlee et al. (1986) Science 232:1629–32.
Brownlee et al. (1986) Diabetes (Suppl. 1):42A (Abstract #166).
Bucala et al. (1992) In: Advances in Pharmacology, vol. 23, pp. 1–34, Academic Press.
Eble et al. (1983) J. Biol. Chem. 258:9406–12.
Hayase et al. (1989) J. Biol. Chem. 263:3758–64.
Nicholls et al. (1989) Lab. Invest. 60:486–91.
Nordbo (1979) J. Dent.Res. 58:1429.
Oimomi et al. (1989) Agric. Biol. Chem. 53:1727–8.
Potts et al. J. Org. Chem. 41:187–91.
Potts et al. (1977) J. Org. Chem. 42:1648–9.
Sell et al. (1989) J. Biol. Chem. 264:21597–602.
Tamura et al. (1977) Synthesis 1:1–17.
Dominianni et al. (1989) J. Med. chem. 32:2301–6.

Primary Examiner—Joseph K. McKane
Attorney, Agent, or Firm—Klauber & Jackson

[57] ABSTRACT

The present invention relates to compositions and methods for inhibiting and reversing nonenzymatic cross-linking (protein aging). Accordingly, compositions are disclosed which comprise an agent capable of inhibiting the formation of advanced glycosylation endproducts of target proteins, and which additionally reverse pre-formed crosslinks in the advanced glycosylation endproducts by cleaving alpha-dicarbonyl-based protein crosslinks present in the advanced glycosylation endproducts. Certain agents useful are thiazolium salts. The method comprises contacting the target protein with the composition. Both industrial and therapeutic applications for the invention are envisioned, as food spoilage and animal protein aging can be treated. A novel immunoassay for detection of the reversal of the nonenzymatic crosslinking is also disclosed.

86 Claims, 2 Drawing Sheets

1. Standard
2. AGE-BSA + PBS
3. AGE-BSA + ALT-766

PREVENTING AND REVERSING THE FORMATION OF ADVANCED GLYCOSYLATION ENDPRODUCTS

CROSS REFERENCE TO RELATED APPLICATIONS

This Application is a continuation-in-part of application U.S. Ser. No. 08/473,104 filed Jun. 7, 1995, now abandoned which is a continuation-in-part of Ser. No. 08/377,155 filed Jan. 18, 1995, now U.S. Pat. No. 5,656,261.

BACKGROUND OF THE INVENTION

The present invention relates generally to the aging of proteins resulting from their reaction with glucose and other reducing sugars, and more particularly to the inhibition of the reaction of nonenzymatically glycosylated proteins and the breaking of cross-linked formed subsequent to formation of advanced glycosylation (glycation) endproducts.

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Further studies have suggested that stored and heat treated foods undergo nonenzymatic browning as a result of the reaction between glucose and the polypeptide chain, and that the proteins are resultingly cross-linked and correspondingly exhibit decreased bioavailability.

This reaction between reducing sugars and food proteins was found to have its parallel in vivo. Thus, the nonenzymatic reaction between glucose and the free amino groups on proteins to form a stable, 1-deoxyketosyl adduct, known as the Amadori product, has been shown to occur with hemoglobin, wherein a rearrangement of the amino terminal of the beta-chain of hemoglobin by reaction with glucose, forms the adduct known as hemoglobin A1c. The reaction has also been found to occur with a variety of other body proteins, such as lens crystallins, collagen and nerve proteins. See Bucala et al., "Advanced Glycosylation; Chemistry, Biology, and Implications for Diabetes and Aging" in *Advances in Pharmacology*, Vol. 23, pp. 1–34, Academic Press (1992).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years. Interestingly, the aging of collagen can be mimicked in vitro by the cross-linking induced by glucose; and the capture of other proteins and the formation of adducts by collagen, also noted, is theorized to occur by a crosslinking reaction, and is believed to account for the observed accumulation of albumin and antibodies in kidney basement membrane.

In U.S. Pat. No. 4,758,583, a method and associated agents were disclosed that served to inhibit the formation of advanced glycosylation endproducts by reacting with an early glycosylation product that results from the original reaction between the target protein and glucose.

Accordingly, inhibition was postulated to take place as the reaction between the inhibitor and the early glycosylation product appeared to interrupt the subsequent reaction of the glycosylated protein with additional protein material to form the cross-linked late-stage product. One of the agents identified as an inhibitor was aminoguanidine, and the results of further testing have borne out its efficacy in this regard.

While the success that has been achieved with aminoguanidine and similar compounds is promising, a need continues to exist to identify and develop additional inhibitors that broaden the availability and perhaps the scope of this potential activity and its diagnostic and therapeutic utility. A further need exists to find agents which not only inhibit this reaction and its consequences, but agents capable of breaking the crosslinks formed as a result of pre-existing advanced glycosylation endproducts, thereby reversing the resultant effects thereof.

SUMMARY OF THE INVENTION

In accordance with the present invention, a method and compositions are disclosed for the inhibition of formation of advanced glycosylation of proteins (protein aging) and for breaking the cross-links that form between advanced glycosylation (glycation) endproducts (AGEs) or between AGEs and other proteins. Advanced glycosylation (glycation) endproducts and cross-linking caused by other reactive sugars present in vivo or in foodstuffs, including ribose, galactose and fructose would also be prevented and reversed by the methods and compositions of the present invention.

In particular, the compositions comprise agents for inhibiting the formation of and reversing the pre-formed advanced glycosylation (glycation) endproducts and breaking the subsequent cross-links. While not wishing to be bound by any theory, it is believed that the breaking of the pre-formed advanced glycosylation (glycation) endproducts and cross-links is a result of the cleavage of α dicarbonyl-based protein crosslinks present in the advanced glycosylation endproducts. The methods and compositions of this invention are thus directed to agents which, by their ability to effect such cleavage, can be utilized to break the pre-formed advanced glycosylation endproduct and cross-link, and the resultant deleterious effects thereof, both in vitro and in vivo.

Certain of the agents useful in the present invention are members of the class of compounds known as thiazoliums.

The agents comprise thiazolium compounds having the following structural formula:

wherein $R^1$ and $R^2$ are independently selected from the group consisting of hydrogen, hydroxy(lower)alkyl, acetoxy (lower)alkyl, lower alkyl, lower alkenyl, or $R^1$ and $R^2$ together with their ring carbons may be an aromatic fused ring, optionally substituted by one or more amino, halo or alkylenedioxy groups;

Z is hydrogen or an amino group;

Y is amino, a group of the formula

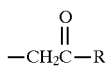

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups; a group of the formula

wherein R' is hydrogen, or a lower alkyl, lower alkynyl, or aryl group; or a group of the formula

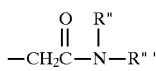

wherein R" is hydrogen and R'" is a lower alkyl group, optionally substituted by an aryl group, or an aryl group, said aryl group optionally substituted by one or more lower alkyl, halo, or alkoxylcarbonyl groups; or R" and R'" are both lower alkyl groups;

X is a halide, tosylate, methanesulfonate or mesitylenesulfonate ion;

and mixtures thereof, and a carrier therefor.

The compounds, and their compositions, utilized in this invention appear to react with an early glycosylation product thereby preventing the same from later forming -the advanced glycosylation end products which lead to cross-links, and thereby, to molecular or protein aging and other adverse molecular consequences. Additionally, they react with already formed advanced glycosylation end products to reduce the amount of such products.

The present invention also relates to a method for inhibiting protein aging and other adverse molecular consequences by contacting the initially glycosylated molecules at the stage of the early glycosylation product with a quantity of one or more of the agents of the present invention, or a composition containing the same, and to a method for breaking the already formed advanced glycosylation end products to reduce the amount of such products by cleaving the a-dicarbonyl-based crosslinks present in the advanced glycosylation endproducts. In the instance where the present method has industrial application, one or more of the agents may be applied to the proteins in question, for instance, either by introduction into a mixture of the same in the instance of a protein extract, or by application or introduction into foodstuffs susceptible to advanced glycation and crosslinking, all to prevent premature aging and spoilage of the particular foodstuffs, and to reverse the effects of already formed advanced glycosylation end products.

The ability to inhibit the formation of advanced glycosylation endproducts, and to reverse the already formed advanced glycosylation products in the body carries with it significant implications in all applications where advanced glycation and concomitant molecular crosslinking is a serious detriment. Thus, in the area of food technology, for instance, the retardation of food spoilage would confer an obvious economic and social benefit by making certain foods of marginal stability less perishable and therefore more available for consumers. Spoilage would be reduced as -would the expense of inspection, removal, and replacement, and the extended availability of the foods could aid in stabilizing their price in the marketplace. Similarly, in other industrial applications where the perishability of proteins is a problem, the admixture of the agents of the present invention in compositions containing such proteins would facilitate the extended useful life of the same. Presently used food preservatives and discoloration preventatives such as sulfur dioxide, known to cause toxicity including allergy and asthma in animals, can be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as a consequence of diabetes. Accordingly, the ability to either retard or substantially inhibit the formation of advanced glycosylation endproducts, and to reduce the amount of cross-links formed between advanced glycosylation endproducts and other proteins in the body carries the promise for treatment of the complications of diabetes and aging for instance, and thereby improving the quality and, perhaps, duration of animal and human life.

The present agents are also useful in the area of personal appearance and hygiene, as they prevent, and reverse, the staining of teeth by cationic anti-microbial agents with anti-plaque properties, such as chlorhexidine.

The invention additionally comprises a novel analytic method for the determination of the "breaking" or reversal of the formation of non-enzymatic endproducts. In this connection, the invention further extends to the identification and use of a novel cross-link structure which is believed to represent a significant number of the molecular crosslinks that form in vitro and in vivo as a consequence of advanced glycation. More particularly, the cross-link structure includes a sugar-derived α-dicarbonyl segment or moiety, such as a diketone, that is capable of cleavage by a dinucleophilic, thiazolium-like compound. Specifically, the cross-link structure may be according to the formula:

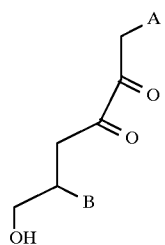

where A and B independently, are sites of attachment to the nucleophilic atom of a biomolecule.

Accordingly, it is a principal object of the present invention to provide a method for inhibiting the formation of advanced glycosylation endproducts and extensive cross-linking of molecules, and a method of breaking the cross-links formed from pre-existing advanced glycosylation endproducts, that occur as a consequence of the reaction of susceptible molecules such as proteins with glucose and other reactive sugars, by correspondingly inhibiting the formation of advanced glycosylation endproducts, and breaking the advanced glycosylation mediated cross-linking that has previously occurred.

It is a further object of the present invention to provide a method as aforesaid which is characterized by a reaction with an initially glycosylated protein identified as an early glycosylation product.

It is a further object of the present invention to provide a method as aforesaid which prevents the rearrangement and cross-linking of the said early glycosylation products to form the said advanced glycosylation endproducts.

It is a yet further object of the present invention to provide agents capable of participating in the reaction with the said early glycosylation products in the method as aforesaid.

It is a yet further object of the present invention to provide agents which break or reverse the advanced glycosylation endproducts formed as a consequence of the aforesaid advanced glycosylation reaction sequence by cleaving the α-dicarbonyl-based protein crosslinks present in the advanced glycosylation endproducts.

It is a still further object of the present invention to provide therapeutic methods of treating the adverse consequences of molecular or protein aging by resort to the aforesaid method and agents.

It is a still further object of the present invention to provide a method of inhibiting, and reversing, the discoloration of teeth by resort to the aforesaid method and agents.

It is a still further object of the present invention to provide compositions, including pharmaceutical compositions, all incorporating the agents of the present invention.

It is still further object of the present invention to provide novel compounds, as well as processes for their preparation, for use in the methods and compositions of the present invention.

It is a still further object of the present invention to provide novel assays which can be utilized to detect compounds having the ability to "break" or reverse the formation of non-enzymatic glycosylation endproducts and their subsequent cross-links.

It is a yet further object of the present invention to provide a cross-link structure that is capable of cleavage by the agents that break or reverse the formation of advanced glycosylation endproducts as set forth herein, and the antibodies specific to said crosslink structure, and the diagnostic and therapeutic uses thereof.

Other objects and advantages will become apparent to those skilled in the art from a consideration of the ensuing description which proceeds with reference to the following illustrative drawings.

BRIEF DESCRIPTION OF THE DRAWING FIGURES

DETAILED DESCRIPTION OF THE PREFERRED EMBODIMENTS

Figure 1:
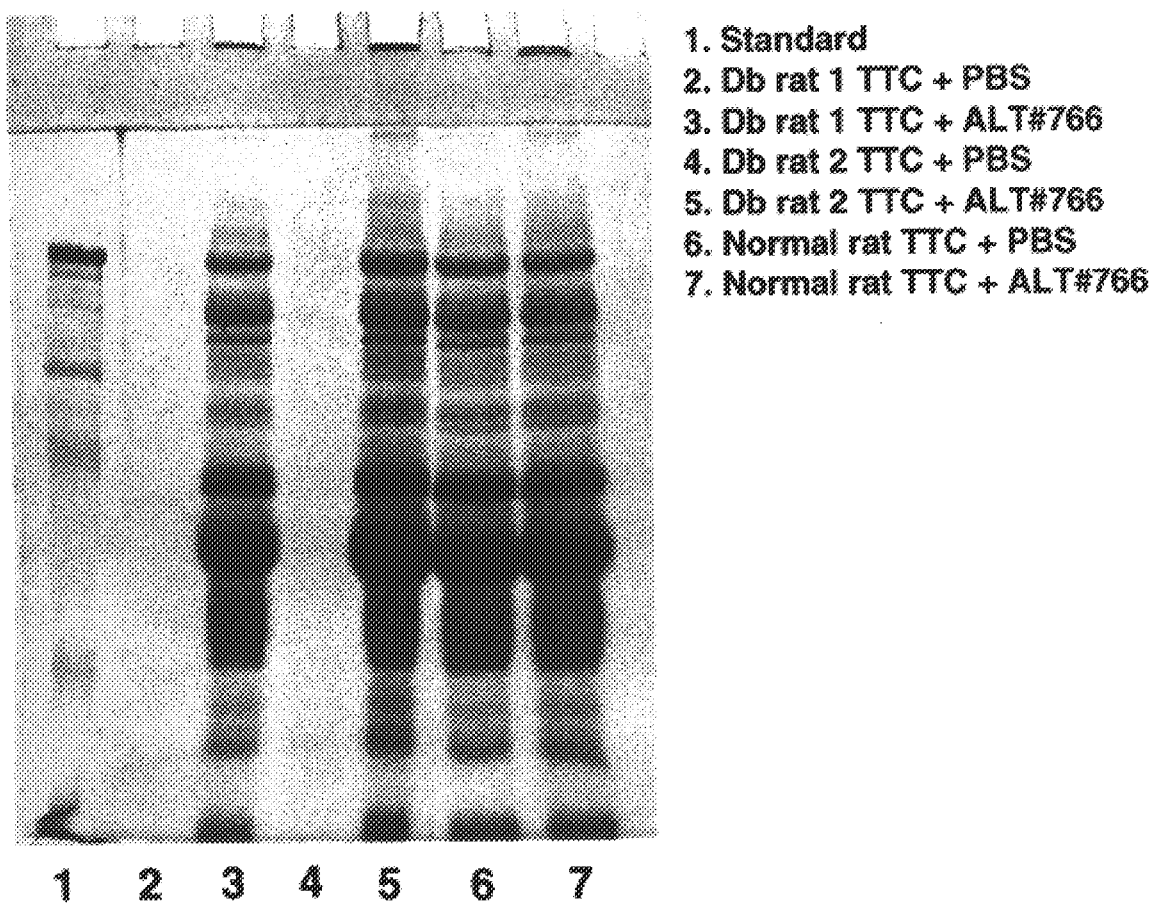
FIG. 1 is an SDS-PAGE gel showing the CNBrr Peptide Maps of Tail Tendon Collagen from Normal and diabetic rates following incubation with 3-(2-phenyl-2-oxoethyl) thiazolium bromide (designated as ALT-766) of the present invention.

In accordance with the present invention, agents, compositions including pharmaceutical compositions containing said agents and associated methods have been developed which are believed to inhibit the formation of advanced glycosylation endproducts in a number of target molecules, including particularly proteins, existing in both animals and plant material, and to reverse the already formed advanced glycosylation endproducts. In particular, the invention relates to a composition which may contain one or more agents comprising compounds having the ability to effect cleavage of α-dicarbonyl-based molecular crosslinks present in the advanced glycosylation endproducts. Useful agents, for instance, comprise compounds having the structural formula:

wherein $R^1$ and $R^2$ are independently selected from the group consisting of hydrogen, hydroxy(lower)alkyl, lower aceloxy(lower)alkyl, lower alkyl, lower alkenyl, or $R^1$ and $R^2$ together with their ring carbons may be an aromatic fused ring, optionally substituted by one or more amino, halo or alkylenedioxy groups;

Z is hydrogen or an amino group;

Y is amino, a group of the formula

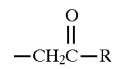

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups; a group of the formula

wherein R' is hydrogen, or a lower alkyl, lower alkynyl, or aryl group; or a group of the formula

wherein R" is hydrogen and R'" is a lower alkyl group, optionally substituted by an aryl group, or an aryl group, said aryl group optionally substituted by one or more lower alkyl, halo, or alkoxylcarbonyl groups; or R" and R'" are both lower alkyl groups;

X is a halide, tosylate, methanesulfonate or mesitylenesulfonate ion;

and mixtures thereof, and a carrier therefor.

The lower alkyl groups referred to above contain 1–6 carbon atoms and include methyl, ethyl, propyl, butyl, pentyl, hexyl, and the corresponding branched-chain isomers thereof. The lower alkynyl groups contain from 2 to 6 carbon atoms. Similarly, the lower alkoxy groups contain from 1 to 6 carbon atoms, and include methoxy, ethoxy, propoxy, butoxy, pentoxy, and hexoxy, and the corresponding branched-chain isomers thereof. These groups are optionally substituted by one or more halo, hydroxy, amino or lower alkylamino groups.

The lower acyloxy(lower)alkyl groups encompassed by the above formula include those wherein the acyloxy portion contain from 2 to 6 carbon atoms and the lower alkyl portion contains from 1 to 6 carbon atoms. Typical acyloxy portions are those such as acetoxy or ethanoyloxy, propanoyloxy, butanoyloxy, pentanoyloxy, hexanoyloxy, and the corresponding branched chain isomers thereof. Typical lower alkyl portions are as described hereinabove.

The aryl groups encompassed by the above formula are those containing 6–10 carbon atoms, such as naphthyl, phenyl and lower alkyl substituted-phenyl, e.g., tolyl and xylyl, and are optionally substituted by 1–2 halo, hydroxy, lower alkoxy or di(lower)alkylamino groups. Preferred aryl groups are phenyl, methoxyphenyl and 4-bromophenyl groups.

The halo atoms in the above formula may be fluoro, chloro, bromo or iodo.

For the purposes of this invention, the compounds of formula (I) are formed as biologically and pharmaceutically acceptable salts. Useful salt forms are the halides, particularly the bromide and chloride, tosylate, methanesulfonate, and mesitylenesulfonate salts. Other related salts can be formed using similarly non-toxic, and biologically and pharmaceutically acceptable anions.

Of the compounds encompassed by Formula I, certain substituents are preferred. For instance, the compounds wherein $R_1$ or $R_2$ are lower alkyl groups are preferred. Also highly preferred are the compounds wherein Y is an amino group, a 2-amino-2-oxoethyl group, a 2-phenyl-2-oxoethyl or a 2-[substituted phenyl]-2-oxoethyl group.

Representative compounds of the present invention are:
3-aminothiazolium mesitylenesulfonate;
3-amino-4,5-dimethylaminothiazolium mesitylenesulfonate;
2,3-diaminothiazolinium mesitylenesulfonate;
3-(2-methoxy-2-oxoethyl)-thiazolium bromide;
3-(2-methoxy-2-oxoethyl)-4,5-dimethylthiazolium bromide;
3-(2-methoxy-2-oxoethyl)-4-methylthiazolium bromide;
3-(2-phenyl-2-oxoethyl)-4-methylthiazolium bromide;
3-(2-phenyl-2-oxoethyl)-4,5-dimethylthiazolium bromide;
3-amino-4-methylthiazolium mesitylenesulfonate;
3-(2-methoxy-2-oxoethyl)-5-methylthiazolium bromide;
3-(2-phenyl-2-oxoethyl)-5-methylthiazolium bromide;
3-[2-(4'-bromophenyl)-2-oxoethyl]thiazolium bromide;
3-[2-(4'-bromophenyl)-2-oxoethyl]-4-methylthiazolium bromide;
3-[2-(4'-bromophenyl)-2-oxoethyl]-5-methylthiazolium bromide;
3-[2-(4'bromophenyl)-2-oxoethyl]-4,5-dimethylthiazolium bromide;
3-(2-methoxy-2-oxoethyl)-4-methyl-5-(2-hydroxyethyl) thiazolium bromide;
3-(2-phenyl-2-oxoethyl)-4-methyl-5-(2-hydroxyethyl) thiazolium bromide;
3-[2-(4'-bromophenyl)-2-oxoethyl]-4-methyl-5-(2-hydroxyethyl)thiazolium bromide;
3,4-dimethyl-5-(2-hydroxyethyl)thiazolium iodide;
3-ethyl-5-(2-hydroxyethyl)-4-methylthiazolium bromide;
3-benzyl-5-(2-hydroxyethyl)-4-methylthiazolium chloride;
3-(2-methoxy-2-oxoethyl)benzothiazolium bromide;
3-(2-phenyl-2-oxoethyl)benzothiazolium bromide;
3-[2-(4'bromophenyl)-2-oxoethyl]benzothiazolium bromide;
3-(carboxymethyl)benzothiazolium bromide;
2,3-(diamino)benzothiazolium mesitylenesulfonate;
3-(2-amino-2-oxoethyl)thiazolium bromide;
3-(2-amino-2-oxoethyl)-4-methylthiazolium bromide;
3-(2-amino-2-oxoethyl)-5-methylthiazolium bromide;
3-(2-amino-2-oxoethyl)-4,5-dimethylthiazolium bromide;
3-(2-amino-2-oxoethyl)benzothiazolium bromide;
3-(2-amino-2-oxoethyl)4-methyl-5-(2-hydroxyethyl) thiazolium bromide;
3-amino-5-(2-hydroxyethyl)-4-methylthiazolium mesitylenesulfonate;
3-(2-methyl-2-oxoethyl)thiazolium chloride;
3-amino-4-methyl-5-(2-acetoxyethyl)thiazolium mesitylenesulfonate;
3-(2-phenyl-2-oxoethyl)thiazolium bromide;
3-(2-methoxy-2-oxoethyl)-4-methyl-5-(2-acetoxyethyl) thiazolium bromide;
3-(2-amino-2-oxoethyl)-4-methyl-5-(2-acetoxyethyl) thiazolium bromide;
2-amino-3-(2-methoxy-2-oxoethyl)thiazolium bromide;
2-amino-3-(2-methoxy-2-oxoethyl)benzothiazolium bromide;
2-amino-3-(2-amino-2-oxoethyl)thiazolium bromide;
2-amino-3-(2-amino-2-oxoethyl)benzothiazolium bromide;
3-[2-(4'-methoxyphenyl)-2-oxoethyl]-thiazolinium bromide;
3-[2-(2',4'-dimethoxyphenyl)-2-oxoethyl]-thiazolinium bromide;
3-[2-(4'-fluorophenyl)-2-oxoethyl]-thiazolinium bromide;
3-[2-(2',4'-difluorophenyl)-2-oxoethyl]-thiazolinium bromide;
3-[2-(4'-diethylaminophenyl)-2-oxoethyl]-thiazolinium bromide;
3-propargyl-thiazolinium bromide;
3-propargyl-4-methylthiazolinium bromide;
3-propargyl-5-methylthiazolinium bromide;
3-propargyl-4,5-dimethylthiazolinium bromide;
3-propargyl-4-methyl-5-(2-hydroxyethyl)-thiazolinium bromide;
3-(2-[3'-methoxyphenyl]-2-oxoethyl)-thiazolium bromide;
3-(2-[3'-methoxy phenyl]-2-oxoethyl)-4 methyl-5-(2'-hydroxyethyl)-thiazolium bromide;
3-(2-[3'-methoxyphenyl]-2-oxoethyl)-benzothiazolium bromide;
2,3-diamino-4-chlorobenzothiazolium mesitylenesulfonate;
2,3-diamino-4-methyl-thiazolium mesitylenesulfonate;
3-amino-4-methyl-5-vinyl-thiazolium mesitylenesulfonate;
2,3-diamino-6-chlorobenzothiazolium mesitylenesulfonate;
2,6-diamino-benzothiazole dihydrochloride;
2,6-diamino-3[2-(4'-methoxyphenyl)-2-oxoethyl] benzothiazolium bromide;
2,6-diamino-3[2-(3'-methoxyphenyl)-2-oxoethyl] benzothiazolium bromide;
2,6-diamino-3[2-(4'-diethylaminophenyl)-2-oxoethyl] benzothiazolium bromide;
2,6-diamino-3(2-(4'-bromophenyl)-2-oxoethyl] benzothiazolium bromide;
2,6-diamino-3(2-(2-phenyl-2-oxoethyl) benzothiazolium bromide;
2,6-diamino-3[2-(4'-fluorophenyl-2-oxoethyl] benzothiazolium bromide;
3-acetamido-4-methyl-5-thiazolyl-ethyl acetate mesitylenesulfonate;
2,3-diamino-5-methylthiazolium mesitylenesulfonate;
3-[2-(2'-naphthyl)-2-oxoethyl]-4-methyl-5-(2'-hydroxyethyl)-thiazolium bromide;
3-[2-(3',5-4'-di-tert-butyl-4'-hydroxyphenyl)-2-oxoethyl]4-methyl-5-(2'-hydroxyethyl)-thiazolium bromide;
3-[2-(2',6'-dichlorophenethylamino)-2-oxoethyl]-4-methyl-5-(2'-hydroxyethyl)-thiazolium-bromide;
3-[2-dibutylamino-2-oxoethyl]-4-methyl-5-(2'-hydroxyethyl)-thiazolium bromide;
3-[2-4'-carbethoxyanilino)-2-oxoethyl]-4-methyl-5-(2'-hydroxyethyl)-thiazolium bromide;
3-[2-(2',6'-diisopropylanilino)-2-oxoethyl]-4-methyl-5-(2'-hydroxyethyl)-thiazolium bromide;

3-amino-4-methyl-5-[2-(2',6'-dichlorobenzyloxy)ethyl]-thioazolium mesitylenesulfonate;
3-[2-(4'-carbmethoxy-3'-hydroxyanilino)-2-oxoethyl]-4-methyl-5-(2'-hydroxyethyl)-thiazolium bromide;
2,3-diamino-4,5-dimethylthiazolium mesitylene sulfonate;
2,3-diamino-4-methyl-5-hydroxyethyl-thiazolium mesitylene sulfonate;
2,3-diamino-5-(3',4'-trimethylenedioxy phenyl)-thiazolium mesitylene sulfonate;
3-[2-(1',4'-benzodioxan-6-yl)-2-oxoethyl]-4-methyl-5-(2'-hydroxyethyl)-thiazolium bromide;
3-[2-(3',4'-trimethylenedioxyphenyl)-2-oxoethyl]-4-methyl-5-(2'-hydroxyethyl)-thiazolium bromide;
3-(2-[1',4-benzodioxan-6-yl]-2-oxoethyl)-thiazolium bromide;
3-[2-(3',4'-trimethylenedioxyphenyl)-2-oxoethyl]-thiazolium bromide;
3-[2-(3',5'-di-tert-butyl-4'-hydroxyphenyl)-2-oxoethyl]-thiazolium bromide;
3-[2-(3',5'-di-tert-butyl-4'-hydroxyphenyl)-2-oxoethyl]-4-methyl-thiazolium bromide;
3-[2-(3',5'-di-tert-butyl-4'-hydroxyphenyl)-2-oxoethyl]-5-methyl-thiazolium bromide;
3-[2-(3',5'-di-tert-butyl-4'-hydroxyphenyl)-2-oxoethyl]-4,5-dimethyl-thiazolium bromide;
3-[2-(3',5'-di-tert-butyl-4'-hydroxyphenyl)-2-oxoethyl]-benzothiazolium bromide;
3-[2-(4'-n-pentylphenyl)-2-oxoethyl]-thiazolinium bromide;
3-[2-(4'-n-pentylphenyl)-2-oxoethyl]-4-methyl-5-(2'-hydroxyethyl)-thiazolinium bromide;
3-[2-4'-diethylaminophenyl)-2-oxoethyl]-4-methyl-5-(2'-hydroxyethyl)-thiazolinium bromide;
3-(2-phenyl-2-oxoethyl)-4-methyl-5-vinyl-thiazolium bromide;
3-[2-(3',5'-tert-butyl-4'-hydroxyphenyl)-2-oxoethyl)-4-methyl-5-vinyl-thiazolium bromide;
3-(2-tert-butyl-2-oxoethyl)-thiazolium bromide
3-(2-tert-butyl-2-oxoethyl)-4-methyl-5-(2'-hydroxyethyl)-thiazolium bromide;
3-(3'-methoxybenzyl)-4-methyl-5-(2'-hydroxyethyl)-thiazolium chloride;
3-(2',6'-dichlorobenzyl)-4-methyl-5-(2'-hydroxyethyl)-thiazolium chloride;
3-(2'-nitrobenzyl)-4-methyl-5-(2'-hydroxyethyl)-thiazolium bromide;
3[2-(4'-chlorophenyl)-2-oxoethyl]-thiazolium bromide;
3[2-(4'-chlorophenyl)-2-oxoethyl]-4-methyl-5-(2'-hydroxyethyl)-thiazolium bromide; and
3[2-(4'-methoxyphenyl)-2-oxoethyl]-4-methyl-5-(2'-hydroxyethyl)-thiazolium bromide.

Certain of the compounds represented by Formula I are novel compounds which represent a further embodiment of the present invention. These compounds are represented by the formula

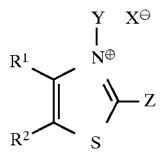
(Ia)

wherein
R¹ and R² are independently selected from the group consisting of hydrogen, hydroxy(lower)alkyl, lower aceloxy(lower)alkyl, lower alkyl, lower alkenyl, or R¹ and R² together with their ring carbons may be an aromatic fused ring, optionally substituted by one or more amino, halo or alkylenedioxy groups;

Z is hydrogen or an amino group;
Y is amino, a group of the formula

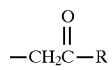

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups; a group of the formula

wherein R' is hydrogen, or a lower alkyl, lower alkynyl, or aryl group; or a group of the formula

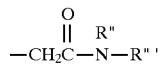

wherein R" is hydrogen and R'" is a lower alkyl group, optionally substituted by an aryl group, or an aryl group, said aryl group optionally substituted by one or more lower alkyl, halo, or alkoxylcarbonyl groups; or R" and R'" are both lower alkyl groups;
with the proviso that at least one of Y and Z is an amino group, and the further proviso that when Y is amino and R₂ and Z are both hydrogen, then R₁ is other than a lower alkyl group; and
X is a halide, tosylate, methanesulfonate or mesitylenesulfonate ion.

Other novel compounds are those of the formula

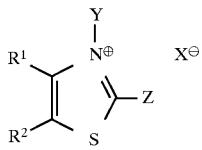

wherein
R¹ and R² are independently selected from the group consisting of hydrogen, hydroxy(lower)alkyl, lower acyloxy(lower)alkyl, lower alkyl, or R¹ and R² together with their ring carbons may be an aromatic fused ring;
Z is hydrogen or an amino group;
Y is an alkynylmethyl group, or a group of the formula

wherein R" is hydrogen and R'" is a lower alkyl group, optionally substituted by an aryl group, or an aryl group, said aryl group optionally substituted by one or more lower alkyl, halo, or alkoxylcarbonyl groups; or R" and R'" are both lower alkyl groups; and
X is a halide, tosylate, methanesulfonate or mesitylenesulfonate ion.

The above compounds are capable of inhibiting the formation of advanced glycosylation endproducts on target molecules, including, for instance, proteins, as well as being capable of breaking or reversing already formed advanced glycosylation endproducts on such proteins. The crosslinking of protein by formation of advanced glycosylation endproducts contributes to the entrapment of other proteins and results in the development in vivo of conditions such as reduced elasticity and wrinkling of the skin, certain kidney diseases, atherosclerosis, osteoarthritis and the like. Similarly, plant material that undergoes nonenzymatic browning deteriorates and, in the case of foodstuffs, become spoiled or toughened and, consequently, inedible, unpalatable or non-nutritious. Thus, the compounds employed in accordance with this invention inhibit this late-stage Maillard effect and intervene in the deleterious changes described above, and reduce the level of the advanced glycosylation endproducts already present in the protein material.

The rationale of the present invention is to use agents which block, as well as reverse, the post-glycosylation step, e.g., the formation of fluorescent chromophores and cross-links, the presence of which is associated with, and leads to adverse sequelae of diabetes and aging. An ideal agent would prevent the formation of such chromophores and of cross-links between protein strands and trapping of proteins onto other proteins, such as occurs in arteries and in the kidney, and reverse the level of such cross-link formation already present.

The chemical nature of the early glycosylation products with which the compounds of the present invention are believed to react may vary, and accordingly the term "early glycosylation product(s)" as used herein is intended to include any and all such variations within its scope. For example, early glycosylation products with carbonyl moieties that are involved in the formation of advanced glycosylation endproducts, and that may be blocked by reaction with the compounds of the present invention, have been postulated. In one embodiment, it is envisioned that the early glycosylation product may comprise the reactive carbonyl moieties of Amadori products or their further condensation, dehydration and/or rearrangement products, which may condense to form advanced glycosylation endproducts. In another scenario, reactive carbonyl compounds, containing one or more carbonyl moieties (such as glycolaldehyde, glyceraldehyde or 3-deoxyglucosone) may form from the cleavage of Amadori or other early glycosylation endproducts, and by subsequent reactions with an amine or Amadori product, may form carbonyl containing advanced glycosylation products such as alkylformyl-glycosylpyrroles.

Several investigators have studied the mechanism of advanced glycosylation product formation. In vitro studies by Eble et al., (1983), "Nonenzymatic Glucosylation and Glucose-dependent Cross-linking of Protein", *J. Biol. Chem.*, 258:9406–9412, concerned the cross-linking of glycosylated protein with nonglycosylated protein in the absence of glucose. Eble et al. sought to elucidate the mechanism of the Maillard reaction and accordingly conducted controlled initial glycosylation of RNase as a model system, which was then examined under varying conditions. In one aspect, the glycosylated protein material was isolated and placed in a glucose-free environment and thereby observed to determine the extent of cross-linking.

Eble et al. thereby observed that cross-linking continued to occur not only with the glycosylated protein but with non-glycosylated proteins as well. One of the observations noted by Eble et al. was that the reaction between glycosylated protein and the protein material appeared to occur at the location on the amino acid side-chain of the protein. Confirmatory experimentation conducted by Eble et al. in this connection demonstrated that free lysine would compete with the lysine on RNase for the binding of glycosylated protein. Thus, it might be inferred from these data that lysine may serve as an inhibitor of advanced glycosylation; however, this conclusion and the underlying observations leading to it should be taken in the relatively limited context of the model system prepared and examined by Eble et al. Clearly, Eble et al. does not appreciate, nor is there a suggestion therein, of the discoveries that underlie the present invention, with respect to the inhibition of advanced glycosylation of proteins both in vitro and in vivo.

The experiments of Eble et al. do not suggest the reactive cleavage product mechanism or any other mechanism in the in vivo formation of advanced glycosylation endproducts in which glucose is always present. In fact, other investigators support this mechanism to explain the formation of advanced glycosylated endproducts in vivo (see for example, Hayase et al, *J. Biol. Chem.*, 263:3758–3764 (1989); Sell and Monnier, *J. Biol. Chem.*, 264:21597–21602 (1989); Oimomi et al., *Agric. Biol. Chem.*, 53(6):1727–1728 (1989); and *Diabetes Research and Clinical Practice*, 6:311–313 (1989). Accordingly, the use of lysine as an inhibitor in the Eble et al. model system has no bearing upon the utility of the compounds of the present invention in the inhibition of advanced glycosylated endproducts formation in the presence of glucose in vivo, and the amelioration of complications of diabetes and aging.

While not wishing to be bound by any particular theory as to the mechanism by which the compounds of the instant invention reverse already formed advanced glycosylation endproducts, studies have been structured to elucidate a possible mechanism. Earlier studies examining the fate of the Amadori product (AP) in vivo have identified one likely route that could lead to the formation of covalent, glucose-derived protein crosslinks. This pathway proceeds by dehydration of the AP via successive beta-eliminations as shown in the Scheme A below. Thus, loss of the 4-hydroxyl of the AP (1) gives a 1,4-dideoxy-1-alkylamino-2,3-hexodiulose (AP-dione) (2). An AP-dione with the structure of an amino-1,4-dideoxyosone has been isolated by trapping model APs with the AGE-inhibitor aminoguanidine. Subsequent elimination of the 5-hydroxyl gives a 1,4,5-trideoxy-1-alkylamino-2,3-hexulos-4-ene (AP-ene-dione) (3), which has been isolated as a triacetyl derivative of its 1,2-enol form. Amadori-diones, particularly the AP-ene-dione, would be expected to be highly reactive toward protein crosslinking reactions by serving as targets for the addition of the amine (Lys, His)-, or sulfhydryl (Cys)-based nucleophiles that exist in proteins, thereby producing stable crosslinks of the form (4).

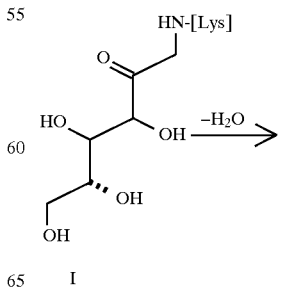

I

-continued

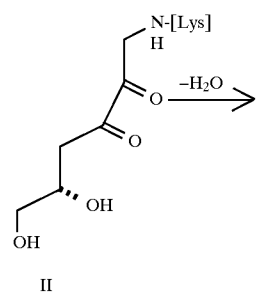

II

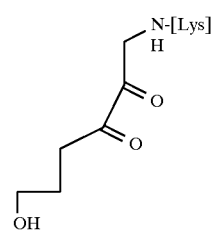

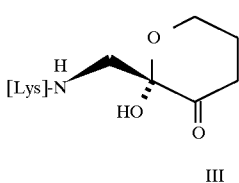

III

-continued

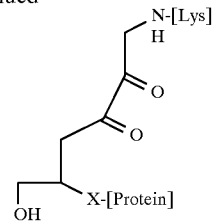

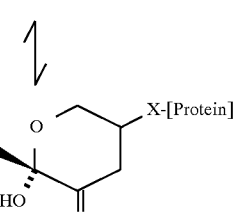

IV

Note that the linear AP-ene-dione of (3) and the stable cross-link of (4) may cyclize to form either 5- or 6-member lactol rings, although only the 6-member cyclic variant is shown in Scheme A set forth above.

The possibility that a major pathway of glucose-derived crosslink formation proceeds through an AP-ene-dione intermediate was investigated by experiments designed to test the occurrence of this pathway in vivo as well as to effect the specific cleavage of the resultant α-dicarbonyl-based protein crosslinks. The thiazolium compounds of the instant invention are thus believed to act as novel "bidentate" nucleophiles, particularly designed to effect a carbon-carbon breaking reaction between the two carbonyls of the crosslink, as shown in Scheme B below under physiological conditions. This scheme shows the reaction of a prototypic α-dione cleaving agent of the formula I, N-phenacylthiazolium bromide, with an AP-ene-dione derived crosslink.

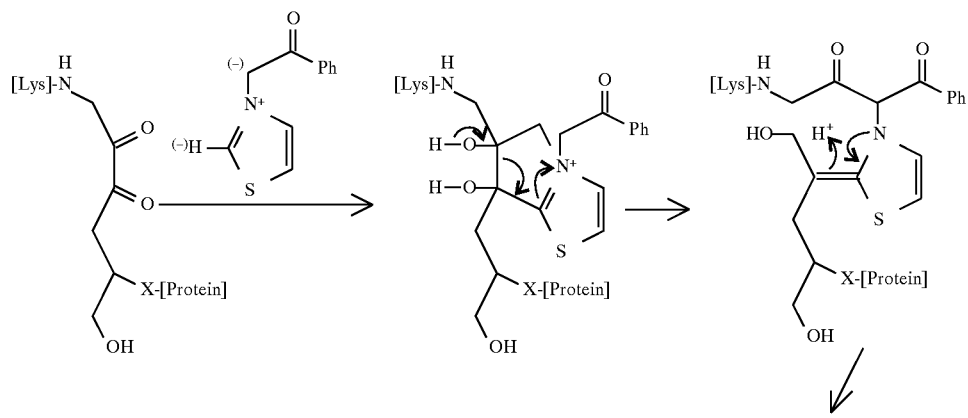

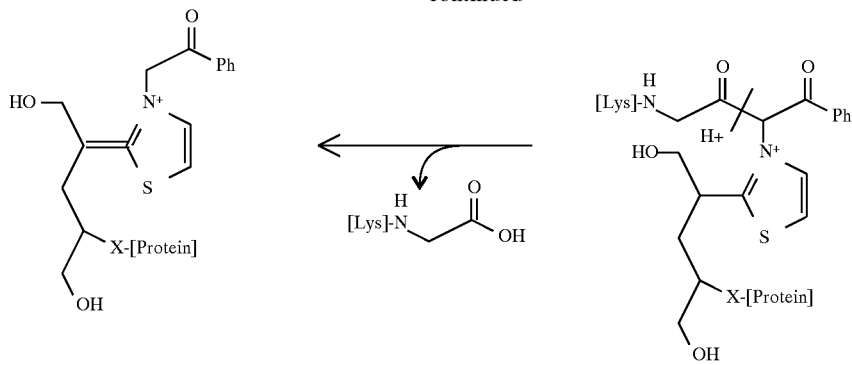

A further experiment to elucidate this reaction involves the reaction of a compound of the formula I, N-phenacylthiazolium bromide, with 1-phenyl-1,2-propanedione to produce the predicted fission product, benzoic acid. The reaction between N-phenacylthiazolium bromide and 1-phenyl-1,2-propanedione was rapid and readily proceeded, confirming this possible mechanism.

Once early, glucose-derived addition products form on proteins, further reactions can ensue to effect a covalent, protein-protein crosslinking reaction. In this regard, a compound of the formula I, N-phenacylthiazolium bromide, was allowed to react with the AGE-crosslinks that form when AGE-modified BSA (AGE-BSA) is allowed to react with unmodified, native collagen. This resulted in a concentration-dependent release of BSA from the preformed AGE-mediated complexes. Again, this study confirmed that a significant portion of the AGE-crosslinks that form under experimental conditions consist of an α-diketone or related structure that is susceptible to cleavage by the advantageous bidentate-type molecules of the compounds of formula I under physiological conditions.

To confirm that the same situation occurs in vivo, isolated collagen from the tail tendons of rats which had been diabetic for 32 weeks were treated with a compound of the formula I, N-phenacylthiazolium bromide, prior to cyanogen bromide digestion and gel electrophoresis analysis. The subsequent electrophoresis revealed that the treated collagen was indistinguishable from untreated, non-diabetic (control) collagen, in marked contrast to the AGE-modified, highly crosslinked, digestion-resistant collagen that is typically isolated from diabetic animals.

The present invention likewise relates to methods for inhibiting the formation of advanced glycosylation endproducts, and reversing the level of already formed advanced glycosylation endproducts, which comprise contacting the target molecules with a composition of the present invention. In the instance where the target proteins are contained in foodstuffs, whether of plant or animal origin, these foodstuffs could have applied to them by various conventional means a composition containing the present agents.

In the food industry, sulfites were found years ago to inhibit the Maillard reaction and are commonly used in processed and stored foods. Recently, however, sulfites in food have been implicated in severe and even fatal reactions in asthmatics. As a consequence, the sulfite treatment of fresh fruits and vegetables has been banned.

The mechanism for the allergic reaction is not known. Accordingly, the present compositions and agents offer a nontoxic alternative to sulfites in the treatment of foods in this manner.

As is apparent from a discussion of the environment of the present invention, the present methods and compositions hold the promise for arresting, and to some extent reversing, the aging of key proteins both in animals and plants, and concomitantly, conferring both economic and medical benefits as a result thereof. In the instance of foodstuffs, the administration of the present composition holds the promise for retarding food spoilage thereby making foodstuffs of increased shelf life and greater availability to consumers. Replacement of currently-used preservatives, such as sulfur dioxide known to cause allergies and asthma in humans, with nontoxic, biocompatible compounds is a further advantage of the present invention.

The therapeutic implications of the present invention relate to the arrest, and to some extent, the reversal of the aging process which has, as indicated earlier, been identified and exemplified in the aging of key proteins by advanced glycosylation and cross-linking. Thus, body proteins, and particularly structural body proteins, such as collagen, elastin, lens proteins, nerve proteins, kidney glomerular basement membranes and other extravascular matrix components would all benefit in their longevity and operation from the practice of the present invention. The present invention thus reduces the incidence of pathologies involving the entrapment of proteins by cross-linked target proteins, such as retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence and tend to occur at an accelerated rate in patients afflicted with diabetes mellitus as a consequence of this hyperglycemia. Thus, the present therapeutic method is relevant to treatment of these and related conditions in patients either of advanced age or those suffering from one of the mentioned pathologies.

Molecular cross-linking through advanced glycosylation product formation can decrease solubility of structural proteins such as collagen in vessel walls and can also trap serum proteins, such as lipoproteins to the collagen. Also, this may result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia has been hypothesized to result from excessive formation of sugar-derived and particularly, glucose-derived cross-links. Such diabetic microvascular changes and microvascular occlusion can be effectively prevented and reversed by chemical inhibition and reversal of the advanced glycosylation product formation utilizing a composition and the methods of the present invention.

Studies indicate that the development of chronic diabetic damage in target organs is primarily linked to hyperglycemia so that tight metabolic control would delay or even prevent end-organ damage. See Nicholls et al., *Lab. Invest.,* 60, No. 4, p. 486 (1989), which discusses the effects of islet isografting and aminoguanidine in murine diabetic nephropathy. These studies further evidence that aminoguanidine diminishes aortic wall protein cross-linking in diabetic rats and confirm earlier studies by Brownlee et al., *Science,* 232:1629–1632 (1986) to this additional target organ of complication of diabetes. Also, an additional study showed the reduction of immunoglobulin trapping in the kidney by aminoguanidine (Brownlee et al., *Diabetes,* (1):42A (1986)).

Further evidence in the streptozotocin-diabetic rat model that aminoguanidine administration intervenes in the development of diabetic nephropathy was presented by Brownlee et al., 1988, supra, with regard to morphologic changes in the kidney which are hallmarks of diabetic renal disease. These investigators reported that the increased glomerular basement membrane thickness, a major structural abnormality characteristic of diabetic renal disease, was prevented with aminoguanidine.

Taken together, these data strongly suggest that inhibition and reversal of the formation of advanced glycosylation endproducts (AGEs), by the teaching of the present invention, may prevent, as well as to some extent reverse late, as well as early, structural lesions due to diabetes, as well as changes during aging caused by the formation of AGEs.

Diabetes-induced changes in the deformability of red blood cells, leading to more rigid cell membranes, is another manifestation of cross-linking and aminoguanidine has been shown to prevent it in vivo. In such studies, New Zealand White rabbits, with induced, long-term diabetes are used to study the effects of a test compound on red blood cell (RBC) deformability (df). The test compound is administered at a rate of 100 mg/kg by oral gavage to diabetic rabbits.

A further consequence of diabetes is the hyperglycemia-induced matrix bone differentiation resulting in decreased bone formation usually associated with chronic diabetes. In animal models, diabetes reduces matrix-induced bone differentiation by 70%.

In the instance where the compositions of the present invention are utilized for in vivo or therapeutic purposes, it may be noted that the compounds or agents used therein are biocompatible. Pharmaceutical compositions may be prepared with a therapeutically effective quantity of the agents or compounds of the present invention and may include a pharmaceutically acceptable carrier, selected from known materials utilized for this purpose. Such compositions may be prepared in a variety of forms, depending on the method of administration. Also, various pharmaceutically acceptable addition salts of the compounds of Formula I may be utilized.

A liquid form would be utilized in the instance where administration is by intravenous, intramuscular or intraperitoneal injection. When appropriate, solid dosage forms such as tablets, capsules, or liquid dosage formulations such as solutions and suspensions, etc., may be prepared for oral administration. For topical or dermal application to the skin or eye, a solution, a lotion or ointment may be formulated with the agent in a suitable vehicle such as water, ethanol, propylene glycol, perhaps including a carrier to aid in penetration into the skin or eye. For example, a topical preparation could include up to about 10% of the compound of Formula I. Other suitable forms for administration to other body tissues are also contemplated.

In the instance where the present method has therapeutic application, the animal host intended for treatment may have administered to it a quantity of one or more of the agents, in a suitable pharmaceutical form. Administration may be accomplished by known techniques, such as oral, topical and parenteral techniques such as intradermal, subcutaneous, intravenous or intraperitoneal injection, as well as by other conventional means. Administration of the agents may take place over an extended period of time at a dosage level of, for example, up to about 30 mg/kg.

As noted earlier, the invention also extends to a method of inhibiting and reversing the discoloration of teeth resulting from nonenzymatic browning in the oral cavity which comprises administration to a subject in need of such therapy an amount effective to inhibit and reverse the formation of advanced glycosylation endproducts of a composition comprising an agent of structural Formula I.

The nonenzymatic browning reaction which occurs in the oral cavity results in the discoloration of teeth. Presently used anti-plaque agents accelerate this nonenzymatic browning reaction and further the staining of the teeth. Recently, a class of cationic anti-microbial agents with remarkable anti-plaque properties have been formulated in oral rinses for regular use to kill bacteria in the mouth. These agents, the cationic antiseptics, include such agents as alexidine, cetyl pyridinium chloride, chlorhexidine gluconate, hexetidine, and benzalkonium chloride.

Tooth staining by chlorhexidine and other anti-plaque agents apparently results from the enhancement of the Maillard reaction. Nordbo, *J. Dent. Res.,* 58:1429 (1979) reported that chlorhexidine and benzalkonium chloride catalyze browning reactions in vitro. Chlorhexidine added to mixtures containing a sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products.

In accordance with this method, the compounds of Formula I are formulated into compositions adapted for use in the oral cavity. Particularly suitable formulations are oral rinses and toothpastes incorporating the active agent.

In the practice of this invention, conventional formulating techniques are utilized with nontoxic, pharmaceutically acceptable carriers typically utilized in the amounts and combinations that are well-known for the formulation of such oral rinses and toothpastes.

The agent of Formula I is formulated in compositions in an amount effective to inhibit and reverse the formation of advanced glycosylation endproducts. This amount will, of course, vary with the particular agent being utilized and the particular dosage form, but typically is in the range of 0.01% to 1.0%, by weight, of the particular formulation.

The compounds encompassed by Formula I are conveniently prepared by chemical syntheses well-known in the art. Certain of the compounds encompassed by Formula I are well-known compounds readily available from chemical supply houses and/or are preparable by synthetic methods specifically published therefor. For instance, 3,4-dimethyl-5-(2-hydroxyethyl)thiazolium iodide; 3-ethyl-5-(2-hydroxyethyl)-4-methylthiazolium bromide; 3-benzyl-5-(2- hydroxyethyl)-4-methylthiazolium chloride; and 3-(carboxymethyl)benzothiazolium bromide are obtainable from Aldrich Chem. Co.

Compounds described in the chemical and patent literature or directly preparable by methods described therein and encompassed by Formula I are those such as 3-(2-phenyl-2-oxoethyl)-4-methylthiazolium bromide and 3-benzyl-5-(2-hydroxyethyl)-4-methyl thiazolium chloride [Potts et al., J. Org. Chem., 41:187–191 (1976)].

Certain of the compounds of formula (I) are novel compounds, not heretofore known in the art. These compounds are those represented by the formula Ia $$\underset{R^2}{\overset{R^1}{\diagdown}}\!\!\!\diagup\!\!\!\overset{\overset{Y}{|}}{\underset{S}{N^\oplus}}\!\!\!\diagdown\!\!\!\!\!\!\diagup\!\!\!\!Z \quad X^\ominus \quad (Ia)$$

wherein $R^1$ and $R^2$ are independently selected from the group consisting of hydrogen, hydroxy(lower)alkyl, acetoxy (lower)alkyl, lower alkyl, lower alkenyl, or $R^1$ and $R^2$ together with their ring carbons may be an aromatic fused ring, optionally substituted by one or more amino, halo or alkylenedioxy groups;

Z is hydrogen or an amino group;

Y is amino, a group of the formula $$\overset{O}{\underset{\|}{-CH_2C-R}}$$

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups; a group of the formula $$-CH_2R'$$

wherein R' is hydrogen, or a lower alkyl, lower alkynyl, or aryl group; or a group of the formula $$\overset{O}{\underset{\|}{-CH_2C}}\!-\!\overset{R''}{\underset{|}{N}}\!-\!R'''$$

wherein R" is hydrogen and R'" is a lower alkyl group, optionally substituted by an aryl group, or an aryl group, said aryl group optionally substituted by one or more lower alkyl, halo, or alkoxylcarbonyl groups; or R" and R' are both lower alkyl groups;

with the proviso that at least one of Y and Z is an amino group, and the further proviso that when Y is amino and $R_2$ and Z are both hydrogen, then $R_1$ is other than a lower alkyl group; and X is a halide, tosylate, methanesulfonate or mesitylenesulfonate ion.

Other novel compounds are those of formula I wherein Y is a lower alkynylmethyl group or a group of the formula $$\overset{O}{\underset{\|}{-CH_2C}}\!-\!\overset{R''}{\underset{|}{N}}\!-\!R'''$$

wherein R" is hydrogen and R'" is a lower alkyl group, optionally substituted by an aryl group, or an aryl group, said aryl group optionally substituted by one or more lower alkyl, halo, or alkoxylcarbonyl groups; or R" and R'" are both lower alkyl groups.

The compounds of formula I wherein Y is a group of the formula $$\overset{O}{\underset{\|}{-CH_2C-R}}$$

wherein R is a lower alkyl, alkoxy, hydroxy, amino or aryl group; or a group of the formula $$-CH_2R'$$

wherein R' is hydrogen, or a lower alkyl, lower alkynyl or aryl group;

X is a halide, tosylate, methanesulfonate or mesitylenesulfonate ion;

can be prepared according to the methods described in Potts et al., J. Org. Chem., 41:187 (1976); and Potts et al., J. Org. Chem., 42:1648 (1977), or as shown in Scheme I below.

Scheme I $$\underset{R^2}{\overset{R^1}{\diagdown}}\!\!\!\diagup\!\!\!\overset{\overset{H}{|}}{\underset{S}{N}}\!\!\!\diagdown\!\!\!\!\!\!\diagup\!\!\!\!Z + XCH_2\overset{O}{\overset{\|}{C}}R \xrightarrow{EtOH} \underset{R^2}{\overset{R^1}{\diagdown}}\!\!\!\diagup\!\!\!\overset{\overset{CH_2\overset{O}{\overset{\|}{C}}-R}{|}}{\underset{S}{N^\oplus}}\!\!\!\diagdown\!\!\!\!\!\!\diagup\!\!\!\!Z \quad X^\ominus$$

(II)        (III)                    (I)

wherein $R^1$, $R^2$, Z, and R are as hereinabove defined, and X is a halogen atom.

In reaction Scheme I, the appropriate substituted thiazole compound of formula II wherein $R^1$, $R^2$ and Z are as hereinbefore defined, is reacted with the appropriate halo compound of formula III wherein R and X are as hereinbefore defined, to afford the desired compound of formula I wherein $R^1$, $R^2$, Z, R and X are as hereinbefore defined.

Typically, this reaction is conducted at reflux temperatures for times of about 1–3 hours. Typically, a polar solvent such as ethanol is utilized for the conduct of the reaction.

The compounds of formula I wherein Y is an amino group can be prepared according to the methods described in Tamura et al., Synthesis, 1 (1977), or as shown below in Scheme II.

SCHEME II

wherein R¹, R² and Z are as defined hereinabove.

In the reaction shown in Scheme II, typically conducted in an anhydrous polar solvent at room temperatures, typical reaction temperatures range from room temperature to reflux, and typical times vary from 1 to about 4 hours. This reaction affords the mesitylene sulfonate, which can then be optionally converted to other thiazolium salts by typical exchange reactions.

The present invention also involves a novel sandwich enzyme immunoassay used to ascertain the ability of test compounds to "break" or reverse already formed advanced glycosylation endproducts by detecting the breaking of AGE (Advanced glycosylation endproduct) moieties from AGE-crosslinked protein. This assay comprises:

a) incubation of AGE-modified bovine serum albumin (AGE-BSA) on collagen-coated wells of microtiter plates for a period of 2–6 hours at a temperature of 37° C.

b) washing of the wells with PBS-Tween; c) application of the test compounds to the washed wells of step b;

d) incubation of the test compounds applied to the washed wells for an additional 12–24 hours at a temperature of about 37° C.; and e) detection of the AGE-breaking using an antibody raised against AGE-ribonuclease or cross-link breaking with an antibody against BSA.

The following examples are illustrative of the invention.

EXAMPLE 1

3-(2-Methoxy-2-oxoethyl)-thiazolium bromide

Thiazole, (850 mg, 10 mmol), methyl bromoacetate (1.52, 10 mmol) and absolute ethanol (50 ml) were refluxed for 2 hours. On cooling, the salt separated and was recrystallized from absolute ethanol to give the title compound (1.59 g), m.p. 189°–190° C. (dec).

EXAMPLE 2

3-Amino-4,5-dimethylthiazolium mesitylenesulfonate

An ice cold solution of the 4,5-dimethyl thiazole (2,26 g, 20 mmol) in dry dichloromethane (15 ml) was treated dropwise with a solution of o-mesitylenesulfonylhydroxylamine (4.3 g, 20 mmol) in dry dichloromethane (15 ml). After stirring for 2 hours at room temperature, anhydrous ether (10 ml) was added. On cooling, colorless needles of the title product, 3-amino-4,5-dimethyl-thiazolium mesitylenesulfonate, separated (3.48 g), m.p. 165°–168° C.

EXAMPLE 3

Using the procedures described above in Examples 1 and 2, the following compounds are prepared.

3-amino-thiazolium mesitylenesulfonate, m.p. 102°–104° C.
2,3-diamino-thiazolium mesitylenesulfonate, m.p. 173°–175° C. (dec).
3-(2-methoxy-2-oxoethyl)-4,5-dimethylthiazolium bromide, m.p. 184°–185° C. (dec).
3-(2-methoxy-2-oxoethyl)-4-methylthiazolium bromide, m.p. 149°–151° C. (dec).
3-(2-phenyl-2-oxoethyl)-4-methylthiazolium bromide, m.p. 218°–220° C. (dec).
3-(2-phenyl-2-oxoethyl)-4,5-dimethylthiazolium bromide, m.p. 212°–213° C. (dec).
3-amino-4-methyl-thiazolium mesitylene sulfonate, m.p. 143°–144° C.
3-(2-methoxy-2-oxoethyl)-5-methyl-thiazolium bromide, m.p. 193°–194° C. (dec).
3-(2-phenyl-2-oxoethyl)-5-methyl-thiazolium bromide, m.p. 193°–194° C.
3-(2-[4¹-bromophenyl]-2-oxoethyl)-thiazolium bromide, m.p. 269°–270° C. (dec).
3-(2-[4¹-bromophenyl]-2-oxoethyl)-4-methyl-thiazolium bromide, m.p. 248°–249° C. (dec).
3-(2-[4¹-bromophenyl]-2-oxoethyl)-5-methyl-thiazolium bromide, m.p. 216°–217° C.
3-(2-[4¹-bromophenyl]-2-oxoethyl)-4,5-dimethylthiazolium bromide, m.p. 223°–224° C. (dec).
3-(2-methoxy-2-oxoethyl)-4-methyl-5-(2-hydroxyethyl)-thiazolium bromide, m.p. 137°–138° C.
3-(2-phenyl-2-oxoethyl)-4-methyl-5-(2-hydroxyethyl)-thiazolium bromide, m.p. 180°–181° C.
3-(2-[4¹-bromophenyl]-2-oxoethyl)-4-methyl-5-(2-hydroxyethyl)-thiazolium bromide, m.p. 251°–252° C. (dec).
3,4-dimethyl-5-(2-hydroxyethyl)-thiazolium iodide, m.p. 85°–87° C.
3-ethyl-5-(2-hydroxyethyl)-4-methyl thiazolium bromide, m.p. 84°–85° C.
3-benzyl-5-(2-hydroxyethyl)-4-methyl thiazolium chloride, m.p. 144°–146° C.
3-(2-methoxy-2-oxoethyl)-benzothiazolium bromide, m.p. 144°–145° C. (dec).
3-(2-phenyl-2-oxoethyl)-benzothiazolium bromide, m.p. 240°–241° C. (dec).
3-(2-[4¹-bromophenyl]-2-oxoethyl)-benzo-thiazolium bromide, m.p. 261°–262° C. (dec).
3-(carboxymethyl)-benzothiazolium bromide m.p. 250° C. (dec).
2,3-diamino-benzothiazolium mesitylenesulfonate, m.p. 212°–214° C. (dec).
3-(2-amino-2-oxoethyl)-thiazolium bromide, m.p. 205°–206° C.
3-(2-amino-2-oxoethyl)-4-methyl-thiazolium bromide, m.p. 220°–222° C.
3-(2-amino-2-oxoethyl)-5-methyl-thiazolium bromide, m.p. 179°–180° C.
3-(2-amino-2-oxoethyl)-4,5-dimethyl-thiazolium bromide, m.p. 147°–148° C.
3-(2-amino-2-oxoethyl)-benzothiazolium bromide, m.p. 222°–223° C.
3-(2-amino-2-oxoethyl)-4-methyl-5-(2-hydroxyethyl) thiazolium bromide, m.p. 182°–183° C.
3-amino-5-(2-hydroxyethyl)-4-methyl-thiazolium mesitylenesulfonate, m.p. 94°–95° C. (dec).
3-(2-methyl-2-oxoethyl)thiazolium chloride, m.p. 178°–179° C.
3-amino-4-methyl-5-(2-acetoxyethyl)thiazolium mesitylenesulfonate, m.p. 118°–120° C.
3-(2-phenyl-2-oxoethyl)thiazolium bromide, m.p. 217°–218° C.
3-(2-methoxy-2-oxoethyl)-4-methyl-5-(2-acetoxyethyl) thiazolium bromide, m.p. 217°–218° C.
3-(2-amino-2-oxoethyl)-4-methyl-5-(2-acetoxyethyl) thiazolium bromide, m.p. 233°–234° C.

2-amino-3-(2-methoxy-2-oxoethyl)thiazolium bromide, m.p. 191°–192° C.

2-amino-3-(2-methoxy-2-oxoethyl)benzothiazolium bromide, m.p. 236°–237° C.

2-amino-3-(2-amino-2-oxoethyl)thiazolium bromide, m.p. 209°–210° C.

2-amino-3-(2-amino-2-oxoethyl)benzothiazolium bromide, m.p. 234°–235° C.

3-[2-(4'-methoxyphenyl)-2-oxoethyl]-thiazolinium bromide, m.p. 248°–249° C. (dec.);

3-[2-(2',4'-dimethoxyphenyl)-2-oxoethyl]thiaxolinium bromide, m.p. 214°–216° C. (dec.);

3-[2-(4'-fluorophenyl-2-oxoethyl]-thiazolinium bromide, m.p. 209°–210° C. (dec.);

3-[2-(2',4'-difluorophenyl)-2-oxoeethyl]-thiazolinium bromide, m.p. 226°–228° C. (dec.);

3-[2-(4'-diethylaminophenyl)-2-oxoethyl]-thiazolinium bromide, m.p. 233°–235° C. (dec.);

3-propargyl-thiazolium bromide, m.p. 64°–66° C.;

3-Propargyl-4-methyl thiazolium bromide, m.p. 213°–215° C.;

3-Propargyl-5-methyl thiazolium bromide, m.p. 127°–129° C.;

3-Propargyl-4,5-dimethyl thiazolium bromide, m.p. 198°–200° C.;

3-Propargyl-4-methyl-5-(2-hydroxyethyl)-thiazolium bromide, m.p. 132°–134° C.;

3-(2-[3'-methoxyphenyl]-2-oxoethyl)-thiazolium bromide, m.p. 224°–225° C.;

3-(2-[3'-methoxy phenyl]-2-oxoethyl)-4 methyl-5-(2'-hydroxyethyl)-thiazolium bromide. m.p. 164°–165° C.;

3-(2-[3'-methoxyphenyl]-2-oxoethyl)-benzothiazolium bromide, m.p. 215°–217° C.;

2,3-diamino-4-chlorobenzothiazolium mesitylenesulfonate, m.p. 228°–230° C.;

2,3-diamino-4-methyl-thiazolium mesitylene sulfonate, m.p. 204°–205° C.;

3-amino-4-methyl-5-vinyl-thiazolium mesitylene sulfonate, m.p. 145°–147° C.;

2,3-diamino-6-chlorobenzothiazolium mesitylenesulfonate, m.p. 244°–246° C.;

2,6-diamino-benzothiazole dihydrochloride, m.p. 318°–320° C. (dec.);

2,6-diamino-3[2-(4'-methoxyphenyl)-2-oxoethyl] benzothiazolium bromide, m.p. 243°–245° C. (dec.);

2,6-diamino-3[2-(3'-methoxyphenyl)-2-oxoethyl] benzothiazolium bromide, m.p. 217°–218° C. (dec.);

2,6-diamino-3[2-(4'-diethylaminophenyl)-2-oxoethyl] benzothiazolium bromide, m.p. 223°–225° C. (dec.);

2,6-diamino-3(2-(4'-bromophenyl)-2-oxoethyl] benzothiazolium bromide, m.p. 258°–259° C. (dec.);

2,6-diamino-3(2-(2-phenyl-2-oxoethyl) benzothiazolium bromide, m.p. 208°–210° C. (dec.);

2,6-diamino-3[2-(4'-fluorophenyl-2-oxoethyl] benzothiazolium bromide, m.p. 251°–252° C. (dec.);

3-acetamido-4-methyl-5-thiazolyl-ethyl acetate mesitylenesulfonate, m.p. syrup material;

2,3-diamino-5-methylthiazolium mesitylesulfonate, m.p. 149°–152° C.;

3-[2-(2'-naphthyl)-2-oxoethyl]-4-methyl-5-(2'-hydroxyethyl)-thiazolium bromide, m.p. 219°–220° C.;

3-[2-(3',5'-Di-tert-butyl-4'-hydroxyphenyl)-2-oxoethyl]-4-methyl-5-(2'-hydroxyethyl)-thiazolium bromide, m.p. 206°–207° C.;

3-[2-(2',6'-Dichlorophenethylamino)-2-oxoethyl]-4-methyl-5-(2'-hydroxyethyl)-thiazolium-bromide, m.p. 193°–195° C.;

3-[2-Dibutylamino-2-oxoethyl]-4-methyl-5-(2'-hydroxyethyl)-thiazolium bromide, m.p. 78°–80° C.;

3-[2-4'-carbethoxyanilino)-2-oxoethyl]-4-methyl-5-(2'-hydroxyethyl)-thiazolium bromide, m.p. 204°–206° C.;

3-[2-(2',6'-Diisopropylanilino)-2-oxoethyl]-4-methyl-5-(2'-hydroxyethyl)-thiazolium bromide, m.p. 166°–168° C.;

3-amino-4-methyl-5-[2(2',6'-dichlorobenzyloxy)ethyl]-thioazolium mesitylenesulfonate, m.p. 164°–166° C.;

3-[2-(4'-carbmethoxy-3'-hydroxyanilino)-2-oxoethyl]4-methyl-5-(2'-hydroxyethyl)-thiazolium bromide, m.p. 222°–223° C.;

2,3-Diamino-4,5-dimethyl thiazolium mesitylene sulfonate, m.p. 166°–168° C.;

2,3-Diamino-4-methyl-5-hydroxyethyl-thiazolium mesitylene sulfonate, m.p. 132°–134° C.;

2,3-Diamino-5-(3',4'-trimethylenedioxy phenyl) thiazolium mesitylene sulfonate, m.p. 224°–226° C.;

3-[2-(1',4'-benzodioxan-6-yl)-2-oxoethyl]-4-methyl-5-(2'-hydroxyethyl)-thiazolium bromide, m.p. 196°–198° C.;

3-[2-(3',4'-trimethylenedioxyphenyl)-2-oxoethyl]-4-methyl-5-(2'-hydroxyethyl)-thiazolium bromide, m.p. 164°–166° C.;

3-(2-[1',4-benzodioxan-6-yl]-2-oxoethyl)-thiazolium bromide, m.p. 238°–239° C.;

3-[2-(3',4'-trimethylenedioxyphenyl)-2-oxoethyl]thiazolium bromide, m.p. 246°–248° C. (dec.);

3-[2-(3',5'-di-tert-butyl-4'-hydroxyphenyl)-2-oxoethyl]-thiazolium bromide;

3-[2-(3',5'-di-tert-butyl-4'-hydroxyphenyl)-2-oxoethyl]-4-methyl-thiazolium bromide, m.p. 226°–228° C. (dec.);

3-[2-(3',5'-di-tert-butyl-4'-hydroxyphenyl)-2-oxoethyl]-5-methyl-thiazolium bromide, m.p. 210°–211° C.;

3-[2-(3',5'-di-tert-butyl-4'-hydroxyphenyl)-2-oxoethyl]-4,5-dimethyl-thiazolium bromide, m.p. 243°–244° C. (dec.);

3-[2-(3',5'-di-tert-butyl-4'-hydroxyphenyl)-2-oxoethyl]-benzothiazolium bromide, m.p. 239°–294° C. (dec.);

3-[2-(4'-n-pentylphenyl)-2-oxoethyl]-thiazolinium bromide, m.p. 218°–220° C. (dec.);

3-[2-(4'-n-pentylphenyl)-2-oxoethyl]-4-methyl-5-(2'-hydroxyethyl)-thiazolinium bromide, m.p. 178°–180° C. (dec.);

3-[2-4'-diethylaminophenyl)-2-oxoethyl]-4-methyl-5-(2'-hydroxyethyl)-thiazolinium bromide, m.p. 184°–186° C. (dec.);

3-(2-phenyl-2-oxoethyl)-4-methyl-5-vinyl-thiazolium bromide, m.p. 176°–177° C.;

3-[2-(3',5'-tert-butyl-4'-hydroxyphenyl)-2-oxoethyl)-4-methyl-5-vinyl-thiazolium bromide, m.p. 208°–209° C.;

3-(2-tert-butyl-2-oxoethyl)-thiazolium bromide, m.p. 211°–212° C.;

3-(2-tert-butyl-2-oxoethyl)-4-methyl-5-(2'-hydroxyethyl)-thiazolium bromide, m.p. 186°–187° C.;

3-(3'-methoxybenzyl)-4-methyl-5-(2'-hydroxyethyl) thiazolium chloride, m.p. 135°–136° C.;

3-(2',6'-dichlorobenzyl)-4-methyl-5-(2'-hydroxyethyl) thiazolium chloride, m.p. 192°–194° C.;

3-(2'-nitrobenzyl)-4-methyl-5-(2'-hydroxyethyl)thiazolium bromide, m.p. 215°–216° C.;

3-[2-(4'-chlorophenyl)-2-oxoethyl]-thiazolium bromide, m.p. 239°–241° C. (dec.);

3-[2-(4'-chlorophenyl)-2-oxoethyl]-4-methyl-5-(2'-hydroxyethyl)-thiazolium bromide, m.p. 240°–251° C. (dec.); and 3-[2-(4'-methoxyphenyl)-2-oxoethyl]-4-methyl-5-(2'-hydroxyethyl)-thiazolium bromide, m.p. 229°–231° C. (dec.).

EXAMPLE 4

|  | mg/tablet |
| --- | --- |
| Compound of Formula I | 50 |
| Starch | 50 |
| Mannitol | 75 |
| Magnesium stearate | 2 |
| Stearic acid | 5 |

The compound, a portion of the starch and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearic acid and the balance of the starch are added and the entire mix blended prior to compression on a suitable tablet press. The tablets are compressed at a weight of 232 mg. using a $^{11}\!/_{32}$" punch with a hardness of 4 kg. These tablets will disintegrate within a half hour according to the method described in USP XVI.

EXAMPLE 5

| Lotion | mg/g |
| --- | --- |
| Compound of Formula I | 1.0 |
| Ethyl alcohol | 400.0 |
| Polyethylene glycol 400 | 300.0 |
| Hydroxypropyl cellulose | 5.0 |
| Propylene glycol | to make 1.0 g |

EXAMPLE 6

| Oral Rinse | |
| --- | --- |
| Compound of Formula I: | 1.4% |
| Chlorhexidine gluconate | 0.12% |
| Ethanol | 11.6% |
| Sodium saccharin | 0.15% |
| FD&C Blue No. 1 | 0.001% |
| Peppermint Oil | 0.5% |
| Glycerine | 10.0% |
| Tween 60 | 0.3% |
| Water to | 100% |

EXAMPLE 7

| Toothpaste | |
| --- | --- |
| Compound of Formula I: | 5.5% |
| Sorbitol, 70% in water | 25% |
| Sodium saccharin | 0.15% |
| Sodium lauryl sulfate | 1.75% |
| Carbopol 934, 6% dispersion in | 15% |
| Oil of Spearmint | 1.0% |
| Sodium hydroxide, 50% in water | 0.76% |
| Dibasic calcium phosphate dihydrate | 45% |
| Water to | 100% |

EXAMPLE 8

Cross-Linking Inhibition Assay

The following method was used to evaluate the ability of the compounds of the present invention to inhibit the cross-linking of glycated bovine serum albumin (AGE-BSA) to the rat tail tendon collagen-coated 96-well plate.

The AGE-BSA was prepared by incubating BSA at a concentration of 200 mg per ml with 200 mM glucose in 0.4M sodium phosphate buffer, pH 7.4 at 37° C. for 12 weeks. The glycated BSA was then extensively dialyzed against phosphate buffer solution (PBS) for 48 hours with additional 5 times buffer exchanges. The rat tail tendon collagen coated plate was blocked first with 300 $\mu$l of superbloc blocking buffer (Pierce #37515X) for one hour. The blocking solution was removed from the wells by washing the plate twice with PBS-Tween 20 solution (0.05% Tween 20) using a NUNC-multiprobe or Dynatech ELISA-plate washer. Cross-linking of AGE-BSA (1 to 10 $\mu$g per well depending on the batch of AGE-BSA) to rat tail tendon collagen coated plate was performed with and without the testing compound dissolved in PBS buffer at pH 7.4 at the desired concentrations by the addition of 50 $\mu$l each of the AGE-BSA diluted in PBS or in the solution of test compound at 37° C. for 4 hours. Unbrowned BSA in PBS buffer with or without testing compound were added to the separate wells as the blanks. The un-cross-linked AGE-BSA was then removed by washing the wells three times with PBS-Tween buffer. The amount of AGE-BSA crosslinked to the tail tendon collagen-coated plate was then quantitated using a polyclonal antibody raised against AGE-RNase. After a one-hour incubation period, AGE antibody was removed by washing 4 times with PBS-Tween.

The bound AGE antibody was then detected with the addition of horseradish peroxidase-conjugated secondary antibody—goat anti-rabbit immunoglobulin and incubation for 30 minutes. The substrate of 2,2-azino-di(3-ethylbenzthiazoline sulfonic acid) (ABTS chromogen) (Zymed #00-2011) was added. The reaction was allowed for an additional 15 minutes and the absorbance was read at 410 nm in a Dynatech plate reader.

The % inhibition of each test compound was calculated as follows.

% inhibition =
{[Optical density (without compound) - optical density (with compound)]/optical density (without compound)} × 100%

The IC$_{50}$ values or the inhibition at various concentrations by test compounds is as follows:

| Test Compound | IC$_{50}$ (mM) | Relative Cross-link Inhibition (at 10 mM) |
|---|---|---|
| 3-amino-4, 5-dimethylaminothiazolium mesitylenesulfonate | 2.8 | |
| 2,3-diaminothiazolinium mesitylenesulfonate | >.10 | 27% |
| 3-(2-methoxy-2-oxoethyl)-thiazolium bromide | 0.25 | |
| 3-(2-methoxy-2-oxoethyl)-4,5-dimethylthiazolium bromide | 0.48 | |
| 3-(2-methoxy-2-oxoethyl)-4-methylthiazolium bromide | | 58% |
| 3-(2-phenyl-2-oxoethyl)-4-methylthiazolium bromide | 5.6 | |
| 3-(2-phenyl-2-oxoethyl)-4,5-dimethylthiazolium bromide | | 37% |
| 3-amino-4-methylthiazolium mesitylenesulfonate | | 46% |
| 3-(2-methoxy-2-oxoethyl)-5-methylthiazolium bromide | 3.2 | |
| 3-(2-phenyl-2-oxoethyl)-5-methylthiazolium bromide | 12.6 | |
| 3-[2-(4'-bromophenyl)-2-oxoethyl]-4-methylthiazolium bromide | | 37% |
| 3-[2-(4'-bromophenyl)-2-oxoethyl]-4,5-dimethylthiazolium bromide | 2.92 | |
| 3-(2-methoxy-2-oxoethyl)-4-methyl-5-(2-hydroxyethyl) thiazolium bromide | | 38% |
| 3-(2-phenyl-2-oxoethyl)-4-methyl-5-(2-hydroxyethyl) thiazolium bromide | >10 | 36% |
| 3-[2-(4'-bromophenyl)-2-oxoethyl]-4-methyl-5-(2-hydroxyethyl) thiazolium bromide | 2.95 | |
| 3-(2-methoxy-2-oxoethyl)benzothiazolium bromide | >10 | 35% |
| 3-(carboxymethyl)benzothiazolium bromide | | 16% |
| 2,3-(diamino)benzothiazolium mesitylenesulfonate | 0.0749 | |
| 3-(2-amino-2-oxoethyl)thiazolium bromide | 0.53 | |
| 3-(2-amino-2-oxoethyl)-4-methylthiazolium bromide | 0.7 | |
| 3-(2-amino-2-oxoethyl)-5-methylthiazolium bromide | 0.0289 | |
| 3-(2-amino-2-oxoethyl)-4,5-dimethylthiazolium bromide | 9.9 | |
| 3-(2-amino-2-oxoethyl) benzothiazolium bromide | 0.02 | |
| 3-(2-amino-2-oxoethyl)4-methyl-5-(2-hydroxyethyl)thiazolium bromide | 1.42 | |
| 3-amino-5-(2-hydroxyethyl)-4-methylthiazolium mesitylenesulfonate | $3.6 \times 10^{-5}$ | |
| 3-(2-phenyl-2-oxoethyl)thiazolium bromide | 11.1 | 34% |
| 3-(2-[3'-methoxyphenyl]-2-oxoethyl)-thiazolium bromide | | 29% |
| 2,3-diamino-4-chlorobenzothiazolium mesitylenesulfonate | | 33% |
| 2,3-diamino-4-methyl-thiazolium mesitylene sulfonate | | 40% |
| 3-amino-4-methyl-5-vinyl-thiazolium mesitylene sulfonate | 11.3 | |
| 2,3-diamino-6-chlorobenzothiazolium mesitylenesulfonate | | 23.2 (2 mm) |
| 2,6-diamino-3[2-(4'-methoxyphenyl)-2-oxoethyl] benzothiazolium bromide | | |
| 2,6-diamino-3[2-(4'-bromophenyl)-2-oxoethyl] benzothiazolium bromide | | |
| 2,6-diamino-3[2-(4'-fluorophenyl-2-oxoethyl] benzothiazolium bromide | | |
| 2,3-diamino-5-methylthiazolium mesitylenesulfonate | | |
| 3-[2-(2'-naphthyl)-2-oxoethyl]-4-methyl-5-(2'-hydroxy-ethyl)-thiazolium bromide | | 61% |
| 3-[2-Dibutylamino-2-oxoethyl]-4-methyl-5-(2'-hydroxyethyl)-thiazolium bromide | | 0.8% (10 mm) |
| 3-[2-4'-carbethoxyanilino)-2-oxoethyl]-4-methyl-5-(2'-hydroxyethyl)-thiazolium bromide | | 8.8% (1 mm) |
| 3-[2-(2',6'-Diisopropylanilino)-2-oxoethyl]-4-methyl-5-(2'-hydroxyethyl)-thiazolium bromide | | 19% |
| 3-amino-4-methyl-5-[2(2',6'-dichlorobenzyloxy)ethyl]-thioazolium mesitylenesulfonate | | 26.5% (3 mm) |
| 3-[2-(4'-carbmethoxy-3[40 -hydroxyanilino)-2-oxoethyl]-4-methyl-5-(2[40 -hydroxyethyl)-thiazolium bromide | 1.76 | |
| 2,3-Diamino-4,5-dimethyl thiazolium mesitylene sulfonate | | 39% |
| 2,3-Diamino-4-methyl-5-hydroxyethyl-thiazolium mesitylene sulfonate | | 18% |
| 2,3-Diamino-5-(3','-trimethylenedioxy phenyl)-thiazolium mesityiene sulfonate | | 40% @ 3 mM |
| 3-[2-(1',4'-benzodioxan-6-yl)-2-oxoethyl]-4-methyl-5-(2'-hydroxyethyl)-thiazolium bromide | | 13% |
| 3-[2-(3',4'-trimethylenedioxyphenyl)-2-oxoethyl]-4-methyl-5-(2'-hydroxyethyl)-thiazolium bromide | 4.4 | |
| 3-[2-(3',4'-trimethylenedioxyphenyl)-2-oxoethyl]-thiazolium bromide | | 45% |
| 3-[2-(3',5'-di-tert-butyl-4'-hydroxyphenyl)-2-oxoethyl]-4-methyl-thiazolium bromide | | 24% @ 0.3 mM |
| 3-[2-(3',5'-di-tert-butyl-4'-hydroxyphenyl)-2-oxoethyl]-5-methyl-thiazolium bromide | 0.78 | 69% @ 1 mM |

-continued

Inhibition Data

| Test Compound | IC$_{50}$ (mM) | Relative Cross-link Inhibition (at 10 mM) |
|---|---|---|
| 3-[2-(3',5'-di-tert-butyl-4'-hydroxyphenyl)-2-oxoethyl]-4,5-dimethyl-thiazolium bromide | 0.16 | |
| 3-[2-(4'-n-pentylphenyl)-2-oxoethyl]-thiazolinium bromide | | ND |
| 3-[2-(4'-n-pentylphenyl)-2-oxoethyl]-4-methyl-5-(2'-hydroxyethyl)-thiazolinium bromide | 1.53 | 52% @ 3 mM |
| 3-[2-4'-diethylaminophenyl)-2-oxoethyl]-4-methyl-5-(2'-hydroxyethyl)-thiazolinium bromide | 2.8 | |
| 3-(2-phenyl-2-oxoethyl)-4-methyl-5-vinyl-thiazolium bromide | | ND |
| 3-[2-(3',5'-tert-butyl-4'-hydroxyphenyl)-2-oxoethyl)-4-methyl-5-vinyl-thiazolium bromide | | ND |

The above experiments suggest that this type of drug therapy may have benefit in reducing the pathology associated with the advanced glycosylation of proteins and the formation of crosslinks between proteins and other macromolecules. Drug therapy may be used to prevent the increased trapping and crosslinking of proteins that occurs in diabetes and aging which leads to sequelae such as retinal damage, and extravascularly, damage to tendons, ligaments and other joints. This therapy might retard atherosclerosis and connective tissue changes that occur with diabetes and aging. Both topical, oral, and parenteral routes of administration to provide therapy locally and systemically are contemplated.

EXAMPLE 9

Cross-Link Breaking Assay

In order to ascertain the ability of the compounds of the instant invention to "break" or reverse already formed advanced glycosylation endproducts, a novel sandwich enzyme immunoassay was developed which detects breaking of AGE (Advanced glycosylation endproduct) moieties from AGE-crosslinked protein. The assay utilizes collagen-coated 96 well microtiter plates that are obtained commercially. AGE-modified protein (AGE-BSA), prepared, for instance, as in Example 8, above, is incubated on the collagen-coated wells for four hours, is washed off the wells with PBS-Tween and solutions of the test compounds are added. Following an incubation period of 16 hours (370° C.) cross-link-breaking is detected using an antibody raised against AGE-ribonuclease or with an antibody against BSA. Positive results in this assay indicate compounds that are capable of reducing the amount of AGE-BSA previously crosslinked to the collagen by breaking the crosslinks and allowing the liberated material to be flushed away in subsequent washing steps. Details of the assay are as follows:

MATERIALS
Immunochemicals and Chemicals
Bovine Serum Albumin (Type V), (BSA) Calbiochem
Dextrose
Superbloc, Pierce, Inc.
Rabbit anti-Bovine Serum Albumin
Horseradish Peroxidase (HRP)-Goat-anti-rabbit), Zymed
HRP substrate buffer, Zymed
ABTS chromogen, Zymed
Phosphate Buffer Saline
Tween 20, Sigma Equipment
ELISA Plate Washer, Dynatech
ELISA Plate Reader, Dynatech
Precision Water Bath
Corning digital pH meter
Glassware and Plasticware
Finneppette Multichannel Pipettor, Baxter
Eppendorf pipettes, Baxter
Eppendorf repeater pipette, Baxter
Pipetter tips for Finneppetter, Baxter
Pipetter tips for Eppendorf, Baxter
Glass test tubes, 13×100 mm; Baxter
Mylar Sealing Tape for 96 well plates, Corning
Biocoat Cellware Rat Tail Collagen Type-1 coated 96-well
plates, Collaborative Biomedical Products METHODS
Preparation of solutions and buffers
1. AGE-BSA stock solutions were prepared as follows. Sodium phosphate buffer (0.4M) was prepared by dissolving. 6 grams of monobasic sodium phosphate in 100 ml of distilled water, 7 grams of dibasic sodium phosphate (0.4M) in 100 ml of distilled water and adjusting the pH of the dibasic solution to 7.4 with the monobasic solution. Sodium azide (0.02 grams) was added per 100 ml volume to inhibit bacterial growth. The BSA solution was prepared as follows: 400 mg of Type V BSA (bovine serum albumin) was added for each ml of sodium phosphate buffer (above). A 400 mM glucose solution was prepared by dissolving 7.2 grams of dextrose in 100 ml of sodium phosphate buffer (above). The BSA and glucose solutions were mixed 1:1 and incubated at 37° C. for 12 weeks. The pH of the incubation mixture was monitored weekly and adjusted to pH 7.4 if necessary. After 12 weeks, the AGE-BSA solution was dialyzed against PBS for 48 hours with four buffer changes, each at a 1:500 ratio of solution to dialysis buffer. Protein concentration was determined by the micro-Lowry method. The AGE-BSA stock solution was aliquoted and stored at −20° C. Dilute solutions of AGE-BSA were unstable when stored at −20° C.

2. Working solutions for crosslinking and breaking studies were prepared as follows. Test compounds were dissolved in PBS and the pH was adjusted to pH 7.4 if necessary. AGE-BSA stock solution was diluted in PBS to measure maximum crosslinking and in the inhibitor solution for testing inhibitory activity of compounds. The concentration of AGE-BSA necessary to achieve the optimum sensitivity was determined by initial titration of each lot of AGE-BSA.

3. Wash buffer ("PBS-Tween") was prepared as follows. PBS was prepared by dissolving the following salts in one liter of distilled water: NaCl, 8 grams; KCl, 0.2 gram; $KH_2PO_4$.1.15 grams; $NaN_3$, 0.2 gram. Tween-20 was added to a final concentration of 0.05% (vol/vol).

4. Substrates for detection of secondary antibody binding were prepared by diluting the HRP substrate buffer 1:10 in distilled water and mixing with ABTS chromogen 1:50 just prior to use.

Assay Procedures

1. Biocoat plates were blocked with 300 $\mu$l of "Superbloc". Plates were blocked for one hour at room temperature and were washed with PBS-Tween three times with the Dynatech platewasher before addition of test reagents.

2. Each experiment was set up in the following manner. The first three wells of the Biocoat plate were used for the reagent blank. Fifty microliters of solutions AGE-BSA were added to test wells in triplicate and only PBS in blank wells. The plate was incubated at 37° C. for four hours and washed with PBS-Tween three times. Fifty microliters of PBS was added to the control wells and 50 $\mu$l of the test "AGE Cross-link breaker" compound was added to the test wells and blank. The plate was incubated overnight (approximately 16 hours) with the test "AGE Cross-link breaker" compound, followed by washing in PBS before addition of primary antibody (below).

3. Each lot of primary antibody, either anti-BSA or anti-RNase, was tested for optimum binding capacity in this assay by preparing serial dilutions (1:500 to 1:2000) and plating 50 $\mu$l of each dilution in the wells of Biocoat plates. Optimum primary antibody was determined from saturation kinetics. Fifty microliters of primary antibody of appropriate dilution, determined by initial titration, was added and incubated for one hour at room temperature. The plate was then washed with PBS-Tween.

4. Plates were incubated with the secondary antibody, HRP-(Goat-anti-rabbit), which was diluted 1:4000 in PBS and used as the final secondary antibody. The incubation was performed at room temperature for thirty minutes.

5. Detection of maximum crosslinking and breaking of AGE crosslinking was performed as follows. HRP substrate (100 ul) was added to each well of the plate and was incubated at 37° C. for fifteen minutes. Readings were taken in the Dynatech ELISA-plate reader. The sample filter was set to "1" and the reference filter was set to "5".

STANDARD OPERATING PROCEDURE

Preliminary Steps

1. Titrate each new lot of AGE-BSA preparation as described in Table 4 and determine the optimum AGE-BSA concentration for the ELISA assay from saturation kinetics.

2. At the beginning of the day, flush the plate washer head with hot water, rinse with distilled water and 50% ethanol. Fill the buffer reservoir of the plate washer with PBS-Tween (0.05%) and purge the system three times before use.

3. Prepare an assay template for setting up the experiment as described under "Assay Setup", #2, below.

Assay Setup

1. Warm Superbloc reagent to 37° C. Add 300 $\mu$l of Superbloc to each well of the Biocoat plate and let stand for sixty minutes at 37° C. Wash the wells three times with PBS-Tween (0.05%). Turn the plate 180 degrees and repeat this wash cycle.

2. Dilute the AGE-BSA in PBS so that 50 $\mu$l of the diluted sample will contain the amount of AGE-BSA necessary for minimum crosslinking and inhibition by pimagedine (aminoguanidine), as determined by initial titration described above. Prepare negative controls by dissolving non-browned BSA in PBS at the same concentration as the AGE-BSA. Add 50 $\mu$l of AGE-BSA or BSA to each well which correspond to the "AGE-BSA" and "BSA" labels on the template.

3. Dissolve the test compounds in PBS at 30 mM concentration for preliminary evaluation. The pH must be checked and adjusted to 7.4 when necessary. Pretreat the collagen-coated plates with AGE-BSA to obtain maximum crosslinking. Prepare negative controls for inhibition experiments by dissolving BSA in the inhibition solution at the same protein concentration as that used for AGE-BSA. Add 50 $\mu$l of AGE-BSA or BSA in the inhibitor solutions to the wells which correspond to "ALT#+AGE-BSA" and to "ALT# blank", respectively, on the template. Incubate the plate at 37° C. for four hours. Following covalent binding of AGE-BSA to the plates, wash the plates with PBS-Tween in preparation of the detection reaction (below).

4. Binding of primary antibody to the Biocoat plates is carried out as follows. At the end of the four hour incubation, the wells are washed with PBS-Tween. Appropriate dilutions (as determined by initial titration) of the rabbit-anti-AGE-RNase or rabbit-anti-BSA antibodies were prepared in PBS, and 50 $\mu$l is added to each well and the plate is allowed to stand at room temperature for sixty minutes.

5. Secondary antibody binding wells are washed with PBS-Tween and 50 microliters HRP (Horseradish Periodase) (Goat anti-rabbit serum) diluted to 1–4000 in PBS and is added to each well. The plate is allowed to stand at room temperature for 30 minutes.

6. Color development was carried out as follows. Plates are washed as in Step 4 above. Dilute the HRP-substrate buffer 1:10 in water. Add 200 $\mu$l of ABTS solution, mix well and add 100 $\mu$l of this reagent to each well. Incubate the plate at 37° C. for 15 minutes. Read the optical density at 410 nm with the sample filter set to "1" and the reference filter set to "5" on the Dynatech ELISA plate reader. Calculate the percent inhibition by the compound as described above. Compounds which are found to reduce the amount of immunoreactivity are considered to be therapeutically useful insofar as they reverse and reduce the levels of advanced glycosylation endproducts.

| Test Compound | $IC_{50}$ (mM) Anti-AGE/Anti-BSA | Breaking Anti-AGE/Anti-BSA (at mM) |
|---|---|---|
| 3-aminothiazolium mesitylenesulfonate | 0.005/3.0 | 71%/67% (30) |
| 3-amino-4, 5-dimethylaminothiazolium mesitylenesulfonate | | 63%/44% (10) |
| 2,3-diaminothiazolinium mesitylenesulfonate | 0.28/0.18 | 79%/90% (10) |
| 3-(2-methoxy-2-oxoethyl)-thiazolium bromide | | 38%/41% (30) |
| 3-(2-methoxy-2-oxoethyl)-4,5-dimethylthiazolium bromide | | 63%/47% (30) |
| 3-(2-methoxy-2-oxoethyl)-4-methylthiazolium bromide | | 54%/51% (30) |
| 3-(2-phenyl-2-oxoethyl)-4-methylthiazolium bromide | 0.23/0.30 | 68%/66% (30) |
| 3-(2-phenyl-2-oxoethyl)-4,5-dimethylthiazolium bromide | | 56%/ND (30) |

-continued

| Test Compound | IC$_{50}$ (mM) Anti-AGE/Anti-BSA | Breaking Anti-AGE/Anti-BSA (at mM) |
|---|---|---|
| 3-amino-4-methylthiazolium mesitylenesulfonate | | 55%/ND (30) |
| 3-(2-methoxy-2-oxoethyl)-5-methylthiazolium bromide | | 72%/27% (30) |
| 3-[2-(4'-bromophenyl)-2-oxoethyl]thiazolium bromide | | 76%/25% (30) |
| 3-(2-phenyl-2-oxoethyl)-4-methyl-5-(2-hydroxyethyl)thiazolium bromide | 14.3/112.0 | 67%/13% (30) |
| 3-benzyl-5-(2-hydroxyethyl)-4-methylthiazolium chloride | 0.42/0.55 | 65%/61% (30) |
| 3-(2-methoxy-2-oxoethyl)benzothiazolium bromide | 1.20/25.9 | 66%/37% (30) |
| 3-(carboxymethyl)benzothiazolium bromide | | 63.7%/17.9% (30) |
| 2,3-(diamino) benzothiazolium mesitylenesulfonate | | 87%/54% (30) |
| 3-(2-amino-2-oxoethyl)-4-methylthiazolium bromide | 4.70/38.6 | 89%/44% (30) |
| 3-(2-amino-2-oxoethyl)-4,5-dimethylthiazolium bromide | | 61%/16% (30) |
| 3-(2-amino-2-oxoethyl)benzothiazolium bromide | 0.4/0.52 | 77%/65% |
| 3-(2-amino-2-oxoethyl) 4-methyl-5-(2-hydroxyethyl)thiazolium bromide | 0.012/0.120 | 65%/57% |
| 3-amino-5-(2-hydroxyethyl)-4-methylthiazolium mesitylenesulfonate | 0.18/0.50 | 76%/48% |
| 3-(2-methyl-2-oxoethyl)thiazolium chloride | 0.83/0.75 | 56%/93% |
| 3-(2-phenyl-2-oxoethyl)thiazolium bromide | 0.020/0.014 | 73%/98% |
| 3-(2-[3'-methoxyphenyl]-2-oxoethyl)-thiazolium bromide | | 22%/44% (10) |
| 2,3-diamino-4-chlorobenzothiazolium mesitylenesulfonate | | 21%/26 (10) |
| 2,3-diamino-4-methyl-thiazolium mesitylenesulfonate | | 25%/30% (10) |
| 3-amino-4-methyl-5-vinyl-thiazolium mesitylenesulfonate | ND/2.0 | 51%/74% (10) |
| 2,3-diamino-6-chlorobenzothiazolium mesitylenesulfonate | | 25%/51 (10) |
| 2,6-diamino-3 [2-(4'-methoxyphenyl)-2-oxoethyl] benzothiazolium bromide | 29%/35% (10) | |
| 2,6-diamino-3 (2-(4'-bromophenyl)-2-oxoethyl] benzothiazolium bromide | | 27%/44% (10) |
| 2,6-diamino-3 [2-(4'-fluorophenyl-2-oxoethyl] benzothiazolium bromide | | 24%/40% (10) |
| 2,3-diamino-5-methylthiazolium mesitylenesulfonate | | 14%/17% (10) |
| 3-[2-(2'-naphthyl)-2-oxoethyl]-4-methyl-5-(2'-hydroxy-ethyl)-thiazolium bromide | | 52%/61% (10) |
| 3-[2-Dibutylamino-2-oxoethyl]-4-methyl-5-(2'-hydroxyethyl)-thiazolium bromide | | 25%/38% (10) |
| 3-[2-4'-carbethoxyanilino)-2-oxoethyl]-4-methyl-5-(2'-hydroxyethyl)-thiazolium bromide | | 48%/57% (10) |
| 3-[2-(2',6'-Diisopropylanilino)-2-oxoethyl]-4-methyl-5-(2'-hydroxyethyl)-thiazolium bromide | | 31%/48% (10) |
| 3-amino-4-methyl-5-[2(2',6'-dichlorobenzyloxy)ethyl]-thioazolium mesitylenesulfonate | | 31%/54% (10) |
| 3-[2-(4'-carbmethoxy-3'-hydroxyanilino)-2-oxoethyl]-4-methyl-5-(2'-hydroxyethyl)-thiazolium bromide | | 24%/18% (10) 24%/23% (10) |
| 2,3-Diamino-4,5-dimethyl thiazolium mesitylene sulfonate mesitylene sulfonate | | 20%/18% (10) |
| 2,3-Diamino-5-(3',4'-trimethylenedioxy phenyl)-thiazolium mesitylene sulfonate | | 13%/42% (1) |
| 3-2-(1',4'-benzodioxan-6-yl)-2-oxoethyl]-4-methyl-5-(2'-hydroxyethyl)-thiazolium bromide | | 11%/21% (3) |
| 3-[2-(3',4'-trimethylenedioxyphenyl)-2-oxoethyl]-4-methyl-5-(2'-hydroxyethyl)-thiazolium bromide | | 34%/0 (10) |
| 3-[2-(3',4'trimethylenedioxyphenyl)-2-oxoethyl]-thiazolium bromide | | 17%/18% (10) |
| 3-[2-(3',5'-ditertbutyl-4'-hydroxyphenyl)-2-oxoethyl]-4-methyl-thiazolium bromide | | 14%/2% (0.3) |
| 3-[2-(3',5'-di-tert-butyl-4'-hydroxyphenyl)-2-oxoethyl]-5-methyl-thiazolium bromide | 3/0.74 | 65%/69% (1) |
| 3-[2-(3',5'-di-tert-butyl-4'-hydroxyphenyl)-2-oxoethyl]-4, 5-dimethyl-thiazolium bromide | | 48%/49% (10) |
| 3-(2-phenyl-2-oxoethyl)-4-methyl-5-vinyl-thiazolium bromide | ND/0.1 | 62%/82% (1) |
| 3-[2-(3',5'-tert-butyl-4'-hydroxyphenyl)-2-oxoethyl)-4-methyl-5-vinyl-thiazolium bromide | ND/0/60% | 32%/50% (0.3) |
| 3-(2-tert-butyl-2-oxoethyl)-thiazolium bromide | | 28%/37% (10) |
| 3-(2-tert-butyl-2-oxoethyl)-4-methyl-5-(2'-hydroxyethyl)-thiazolium bromide | | 4%/19% (10) |
| 3-(3'-methoxybenzyl)-4-methyl-5-(2'-hydroxyethyl)-thiazolium chloride | | 14%/25% (10) |
| 3-(2',6'-dichlorobenzyl)-4-methyl-5-(2'-hydroxyethyl)-thiazolium chloride | | 6%/27% (10) |
| 3-(2'-nitrobenzyl)-4-methyl-5-(2'-hydroxyethyl)-thiazolium bromide | | 11%/13% (10) |

EXAMPLE 10

To ascertain the ability of the compounds of the invention to decrease the amount of IgG crosslinked to circulating red blood cells in streptozotocin-induced diabetic rats, was measured by the following assay. The test compounds are administered to the test animals either orally or intraperitoneally, and the blood samples are collected are tested at various times, e.g. 4, 7 or 19 days, after administration to assess efficacy.

Protocol for RBC-IgG Assay
A. Preparation of Red Blood Cells

Blood is collected from the rats in heparinized tubes and spun at 2000 x g for 10 minutes, and the plasma carefully removed. Then, about 5 ml of PBS per ml blood is added, gently mixed, and then spun again. The supernatant is then removed by aspiration. The wash is then repeated two more times. Then, 0.2 to 0.3 ml of packed RBC is withdrawn from the bottom of the tube, using a pipette, and added to the PBS to make a 1 to 10 dilution. This dilution is then further diluted 1 to 25 and 1 to 50 in PBS.

B. Assay set up.
1. Warm Superbloc to 37° C.
2. Take a plate of Multiscreen-HA, 0.45u. Cellulose ester membrane-sealed 96 well plate (Millipore MAHAS45).
3. Wet the wells with 100 ul of PBS.
4. Add 300 ul of superblock to each well and incubate at 37° C. for one hour.
5. Place the plate on the Milliliter Vacuum holder, turn on the vacuum and press the plate down once for tight hold. The liquids in the wells will be suctioned off. Wash the wells with 300 ul of PBS-Tween 0.05%.
6. Turn off the vacuum and add 100 ul of PBS to each well.
7. Gently vortex the RBC samples and pipette 50 ul to the wells, as per the protocol sheet. Leave first three wells for reagent blanks. Leave another three wells for antibody blank.
8. Suction-off the liquid as above and wash the RBCs twice with PBS.
9. Dilute AP(Rb-anti-rat) (Sigma A-6066), 1 to 25000 in PBS.
10. Add 50 ul to the wells and let stand at room temp. for two hours.
11. Suction-off the liquid as above and wash the RBCs twice with PBS.
12. Add pNPP substrate (1 mg/ml in DEA buffer). 100 ul per well.
13. Let the color develop for two hours at 37° C.
14. Place a 96 well corning micrometer plate in the vacuum chamber.
15. Place the sample plate on the vacuum manifold. Make sure the bottom of the plate is completely dry.
16. Apply vacuum for about 5 minutes. Add 100 ul of PBS to all wells and apply vacuum again for 5 minutes. Gently lift the plate and make sure that no liquid drops are hanging at the bottom of the plate. If necessary apply vacuum for few more minutes. Read OD of the solution collected in the Corning plate on Dynatech Plate reader Sample filter 1 and Ref. filter 4.
17. Calculate percent breaking: 100* (OD410 control-OD410 treated)/OD410 control.

Percent inhibition in animals dosed orally at a rate of 10 mg/kg body weight are as listed below:

| | |
|---|---|
| 3-amino-4-methyl-5-vinyl-thiazolium mesitylenesulfonate | 11 ± 1 @ 19 days |
| 3-[2-(2'-naphthyl)-2-oxoethyl]-4-methyl-5-(2'-hydroxyethyl)-thiazolium bromide | 40 ± 24 @ 19 days |
| 3-[2-(3',5'-di-tert-butyl-4'-hydroxy-phenyl)-2-oxoethyl]-5-methyl-thiazolium bromide | 65 ± 15 @ 19 days |
| 3-(2-phenyl-2-oxoethyl)-4-methyl-5-vinyl-thiazolium bromide | 58 ± 21 @ 19 days |

The extensive degree of reversal of crosslinking observed in these studies underscores two important conclusions by Applicants. First, a large percentage of cross-links formed in vivo are susceptible to attack and cleavage by the dinucleophilic, thiazolium-based compounds of the present invention, and thus, by inference, that these cross-links comprise an α-diketone segment consistent with the model shown in Schemes A and B. Second, the crosslink-breaking agents of the present invention can act catalytically, in the sense that a single, dinucleophilic thiazolium-based molecule of the present invention can attack and cause the cleavage of more than one glycation cross-link.

EXAMPLE 11

This example describes the preparation of CNBr peptide maps of rat laid tendon collagen from normal and diabetic animals following treatment with a compound of formula I, i.e., 3-(2-phenyl-2-oxoethyl)thiazolium bromide (ALT 766). Collagen fibers (5 mg) from streptozotocin diabetic rats and age-matched control animals hydrated in land PBS at 60° C. for one hour, the soluble collagen was removed and the pellets were washed several times with PBS then treated with 3-(2-phenyl-2-oxoethyl)thiazolium bromide at a concentration of 30 mM for 16 hours. Following incubation, the pellets were centrifuged, washed, and treated with CNBr (40 mg/ml in formic acid at 30° C. for 48 hours. The CNBr digests were lyophilized repeatedly to remove CNBr and acid and then subjected to SDS-PAGE (20% acrylamide) under reducing conditions (Lanes 1, 2 and 9, MWS; lane 3, 4 and 5, tail tendon collagen from non-diabetic animals with 3 and 5 treated with 3-(2-phenyl-2-oxoethyl)thiazolium bromide, 4 was treated with PBS; lanes 6,7 and 8, collagen from diabetic animals with 6 and 8 treated with 3-(2-phenyl-2-oxoethyl)thiazolium bromide, 7 was treated with PBS). The gels which result are as shown in FIG. 1.

EXAMPLE 12

Preparation of AGE-BSA and Crosslinked-AGE-BSA

Prepare the following solutions.
1. Buffer: 0.4M sodium phosphate pH 7.4.
   NaH$_2$PO$_4$:6 g/100 ml
   Na$_2$HPO$_4$:7 g/100 ml
   pH of the monbasic sodium phosphate was adjusted to 7.4 with the dibasic 0.02 g sodium axide wa added per 100 ml of the buffer.
2. BSA Solution
   BSA: Calbiochem Type V; 400 mg/ml in the buffer 1. Total volume prepared 50 g/125 ml. Filtered through a 0.45u filter into a sterile one liter Corning flask.
3. Glucose solution. 400 uM
   Glucose: 400 mM 9 g/125 ml of buffer. Filtered through a 0.45u filter into one liter Corning sterile flask.

Reaction setup:

BSA and glucose solutions (100 ml each) were mixed in the one liter Corning sterile flask, screw-capped tight and incubated at 56° C. without shaking. The bottle was opened once a week to remove aliquots for testing. Reaction was continued for 9 weeks when AGE-BSA polymer formation was observed.

Figure 2:
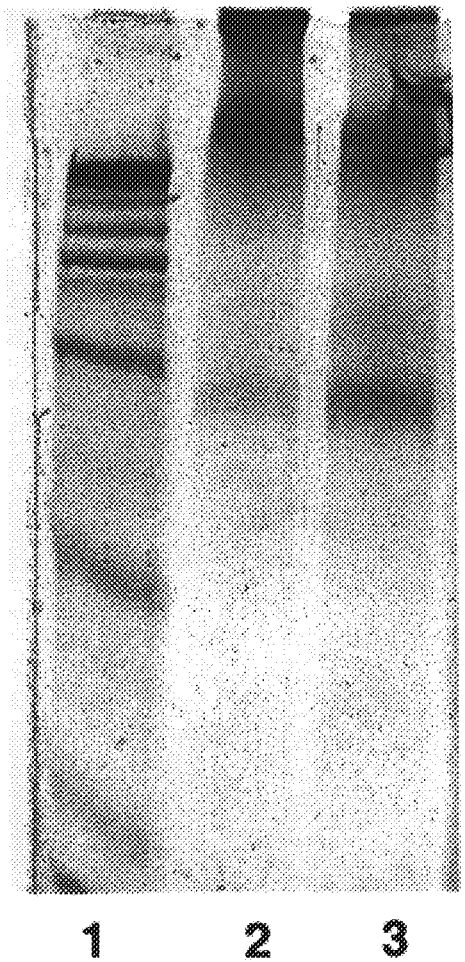
FIG. 2 is an SDS-PAGE gel showing the physical evidence for the breaking of cross-linked AGE-BSA by 3-(2-phenyl-2-oxoethyl)thiazolium bromide, a compound of the present invention.

Breaking the polymer:

Pieces of AGE-BSA gel was washed with PBS until no more protein was leached in the supernatant, blotted dry with paper towels. About 50 mg of the washed gel was incubated either with PBs or 10 mm 3-(2-phenyl-2-oxoethyl)thiazolium bromide (ALT 766) overnight at 37° C. The supernatants were analyzed by SDS-PAGE and stained with coommassie blue. The resulting gels are shown in FIG. 2.

EXAMPLE 13

To further study the ability of AGE crosslink-inhibiting and reversing agents of the present invention to prevent the discoloration of protein on a surface, such as that which occurs on the tooth surface, the following surface browning experiment is performed. As a substitute for a pellicle-covered tooth surface, unexposed and developed photographic paper is used to provide a fixed protein (gelatin, i.e., collagen) surface on a paper backing. Five millimeter circles are punched and immersed for one week at 50° C. in a solution of 100 mM glucose-6-phosphate in a 0.5M phosphate buffer, pH 7.4, containing 3 mM sodium azide. Glucose-6-phosphate is a sugar capable of participating in nonenzymatic browning at a more rapid rate than glucose. In addition to the glucose-6-phosphate, chlorhexidine and/or a compound of Formula I are included. After incubation, the gelatin/paper disks are rinsed with water, observed for brown color, and photographed.

Incubation of the disks in glucose-6-phosphate alone shows slight brown color versus disks soaked in buffer alone. Inclusion of chlorhexidine (in the form of Peridex® at a final concentration of 0.04% chlorhexidine) shows significant browning. Addition of a compound of Formula I to the chlorhexidine completely inhibits browning of the gelatin, as does inclusion of a compound of Formula I in the absence of chlorhexidine.

The slight brown color formed by the action of glucose-6-phosphate on the gelatin surface alone and its prevention by a compound of Formula I demonstrates the utility of the present invention in preventing nonenzymatic browning of tooth surfaces. The enhanced browning in the presence of chlorhexidine and its prevention with a compound of Formula I demonstrates the utility of the present invention in preventing the anti-plaque agent-enhanced nonenzymatic browning which occurs with chlorhexidine.

EXAMPLE 14

As a demonstration of the general utility of compounds of the present invention to break undesired crosslinks in medically relevant biomolecules, Applicants conducted the following experiment with the amyloid peptide of Alzheimer's disease. This 14 kDalton peptide comprises a main constituent of the large, plaque-like aggregates which form within the brain parenchyma of Alzheimer's disease patients. The gradual accumulation of such amyloid plaques, together with other abnormal features such as perivascular amyloid and neurofibrillary tangles, is thought to account for certain of the neurotoxic and other pathogenic processes of this dementia, which is invariably fatal and presently incurable.

The Alzheimer's amyloid peptide is known to accumulate AGE modifications in vivo, and upon exposure to physiologically relevant concentrations of glucose, in vivo, which glycation enhances the formation of insoluble aggregates of the peptide, reminiscent of Alzheimer's amyloid plaques.

AGE-β-peptide was prepared by incubating an aliquot of the soluble β-amyloid peptide, synthetically prepared and corresponding in sequence to the β-amyloid peptide found in the plaques typical of Alzheimer's disease, in a neutral buffered glucose solution for three months, generally as described above for the preparation of AGE-BSA except that β-peptide was substituted for BSA as the glycation substrate. The AGE-β-peptide, glycated and cross-linked after this prolonged exposure to glucose in vivo, was separated from low molecular weight reactants by size exclusion chromatography (e.g. over a PFD-10 column), and iodinated by standard methods to give $^{125}$I-AGE-β-peptide as the desired radiolabeled reagent useful to test or screen compounds for molecular AGE-breaking activity according to the following procedure. Aliquots of $^{125}$I-AGE-β-peptide were incubated with or without added test compounds of the present invention, at predetermined concentrations (e.g., k 10 mM Compound 766) for a predetermined tine (e.g. overnight), after which a sample of the incubation mixture was prepared for denaturing gel electrophoresis (SDS-PAGE) and analyzed to determine apparent molecular weight according to well-known procedures. Autoradiograms exposed on the resulting electrophoresis gels were scanned into a digital radiographic imaging and analysis system which was used to record radioactivity as a function of apparent molecular weight (electrophoretic mobility in SDS-containing buffer). Inspection of the results of this experiment showed that if $^{125}$I-AGE-β-peptide were not exposed to an "AGE-breaker" compound of the present invention, it fluted a high molecular weight (>40 kDalton) band, suggesting that its glycation was accompanied by aggregation and the formation of stable covalent cross-links. If, however, $^{125}$I-AGE-β-peptide was first incubated in a solution of an AGE crosslink-bearing agent of the present invention, the $^{125}$I-AGE-β-peptide was significantly disaggregated as shown by the appearance of low molecular weight (>18 kDalton) iodinated material in the final radiogram. This experiment suggests not only that dinucleophilic thiazolium-like agents of the present invention can be used to hydrolyze covalent AGE-mediated crosslinks between protein strands, but also that such inhibition and reversal of AGEs can reverse the adverse molecular consequences of AGE accumulation on a protein relevant to human disease.

EXAMPLE 15

The cross-link structure and related compounds of the present invention also find utility as antigens or haptens, to elicit antibodies specifically directed thereto. Such antibodies, likewise of the present invention, are useful in turn to identify AAA structures of the present invention. By constructing immunoassays employing anti-cross-link structure antibodies of the present invention, for instance, the degree to which proteins are modified by such cross-links can be measured. As discussed above, and depending on the half-life of the protein so modified, immunochemical measurement of the cross-link epitopes on a protein sample, such as hemoglobin, provides an index of recent AGE-formation. Likewise, immunochemical detection of cross-link epitopes on circulating and/or tissue proteins can be used to monitor the course of therapy with agents of the present invention, which agents are directed toward inhibition of, and breaking of advanced glycation.

Cross-link-modified BSA for use as an immunogen can be prepared by coupling a cross-link structure with bovine serum albumin (BSA) using any of a number of well-known divalent coupling reagents such as a carbodiimide like EDC. Various other haptens, antigens, and conjugated immunogens corresponding to the cross-link structures of the present invention, including without limitation those described specifically herein, can conveniently be prepared, either by isolation from incubation mixtures or by direct synthetic approaches. This cross-structure may then be used as an immunogen to raise a variety of antibodies which recognize specific epitopes or molecular features thereof.

In a preferred embodiment, the cross-link structure itself is considered a hapten, which is correspondingly coupled to any of several preferred carrier proteins, including for instance keyhole limpet hemocyanin (KLH), thyroglobulin, and most preferred, bovine serum albumin (BSA), using a divalent coupling reagents such as EDC, according to protocols widely circulated in the art.

The cross-link structure, whether alone or coupled to a carrier protein, may be employed in any well-recognized immunization protocol to generate antibodies and related immunological reagents that are useful in a number of applications owing to the specificity of the antibodies for molecular features of the cross-link structure.

Following a preferred protocol, any of several animal species may be immunized to produce polyclonal antisera directed against the cross-link structure-protein conjugate, including for instance mice, rats, hamsters, goats, rabbits, and chickens. The first of three of the aforesaid animal species are particularly desired choices for the subsequent production of hybridomas secreting hapten-specific monoclonal antibodies. The production of said hybridomas from spleen cells of immunized animals may conveniently be accomplished by any of several protocols popularly practiced in the art, and which describe conditions suitable for immortalization of immunized spleen cells by fusion with an appropriate cell line, e.g. a myeloma cell line. Said protocols for producing hybridomas also provide methods for selecting and cloning immune splenocyte/myeloma cell hybridomas and for identifying hybridomas clones that stably secrete antibodies directed against the desired epitope(s). Animal species such as rabbit and goat are more commonly employed for the generation of polyclonal antisera, but regardless of whether polyclonal antisera or monoclonal antibodies are desired ultimately, the hapten-modified carrier protein typically is initially administered in conjunction with an adjuvant such as Complete Freund's Adjuvant. Immunizations may be administered by any of several routes, typically intraperitoneal, intramuscular or intradermal; certain routes are preferred in the art according to the species to be immunized and the type of antibody ultimately to be produced. Subsequently, booster immunizations are generally administered in conjunction with an adjuvant such as alum or Incomplete Freund's Adjuvant. Booster immunizations are administered at intervals after the initial immunization; generally one month is a suitable interval, with blood samples taken between one and two weeks after each booster immunization. Alternatively, a variety of so-called hyperimmunization schedules, which generally feature booster immunizations spaced closer together in time, are sometimes employed in an effort to produce anti-hapten antibodies preferentially over anti-carrier protein antibodies.

The antibody titers in post-boost blood samples can be compared for hapten-specific immune titer in any of several convenient formats including, for instance, Ouchterlony diffusion gels and direct ELISA protocols. In a typical direct ELISA, a defined antigen is immobilized onto the assay well surface, typically in a 96-well or microtiter plate format, followed by a series of incubations separated by rinses of the assay well surface to remove unbound binding partners. By way of non-limiting example, the wells of an assay plate may receive a dilute, buffered aqueous solution of the hapten/carrier conjugate, preferably wherein the carrier protein differs from that used to immunize the antibody-producing animal to be tested; e.g. serum from AAA/KLH conjugate-immunized animal might be tested against assays wells decorated with immobilized AAA/BSA conjugate. Alternatively, the assay surface may be decorated by incubation with the hapten alone. Generally, the surface of the assay wells is then exposed to a solution of an irrelevant protein, such as casein, to block unoccupied sites on the plastic surfaces. After rinsing with a neutral buffered solution that typically contains salts and a detergent to minimize non-specific interactions, the well is then contacted with one of a serial dilution of the serum prepared from the blood sample of interest (the primary antiserum). After rinsing again, the extent of test antibodies immobilized onto the assay wells by interact ion with the desired hapten or hapten/carrier conjugate can be estimated by incubation with a commercially available enzyme-antibody conjugate, wherein the antibody portion of this secondary conjugate is directed against the species used to produce the primary antiserum; e.g. if the primary antiserum was raised in rabbits, a commercial preparation of anti-rabbit antibodies raised in goat and conjugated to one of several enzymes, such as horseradish peroxidase, can he used as the secondary antibody. Following procedures specified by the manufacturer, the amount of this secondary antibody can then be estimated quantitatively by the activity of the associated conjugate enzyme in a colorimetric assay. Many related ELISA or radioimmunometric protocols, such as competitive ELISAs or sandwich ELISAs, all of which are well know in the art, may optionally be substituted, to identify the desired antisera of high titer; that is, the particular antisera which give a true positive result at high dilution (e.g. greater than $1/1000$ and more preferably greater than $1/10,000$).

Similar immunometric protocols can be used to estimate the titer of antibodies in culture supernatants from hybridomas prepared from spleen cells of immunized animals. In so characterizing antisera or hybridoma supernatants, it is desirable to employ a variety of control incubations, e.g. with different carrier proteins, related but structurally distinct haptens or antigens, and omitting various reagents in the immunometric procedure in order to minimize non-specific signals in the assay and to identify reliable determinations of antibody specificity and titer from false positive and false negative results. The types of control incubations to use in this regard are well known. Also, the same general immunometric protocols subsequently may be employed with the antisera identified by the above procedures to be of high titer and to be directed against specific structural determinants in the cross-link structures on biological samples, foodstuffs or other comestibles, or other amine-bearing substances and biomolecules of interest. Such latter applications of the desired anti-aldehyde-modified Amadori product antibodies, whether polyclonal or monoclonal, together with instructions and optionally with other useful reagents and diluents, including, without limitation, a set of molecular standards of the cross-link structure, may be provided in kit form for the convenience of the operator.

EXAMPLE 16

Cleavage of a Model α-dione by PTB

1-Phenyl-1,2-propanedione (2.2 equiv) was incubated with 10 mM PTB in 0.5 M pH 7.4 phosphate buffer containing 50% methanol at 37° C. under nitrogen. Aliquots were taken at 1, 2, 4, 23 and 29 hours and analyzed by HPLC on a C18 reverse phase column using a gradient of 25% to 100% of methanol in water. Formation of benzoic acid (i.e., the absorption peak eluting at a retention time identical to a standard preparation of reagent benzoic acid under the same chromatographic conditions) vs. time is shown in FIG. 1. No benzoic acid was released from PTB or the dione when either was incubated in the absence of the other.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A composition for inhibiting the advanced glycosylation of a target protein in the oral cavity, and reversing pre-formed advanced glycosylation crosslinks, comprising an effective amount of a compound selected from the group consisting of compounds of the structural formula:

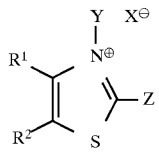

(I)

wherein $R^1$ and $R^2$ are independently selected from the group consisting of hydrogen, hydroxy(lower)alkyl, lower aceloxy(lower)alkyl, lower alkyl, lower alkenyl, or $R^1$ and $R^2$ together with their ring carbons may be an aromatic fused ring, optionally substituted by one or more amino, halo or alkylenedioxy groups;

Z is hydrogen or an amino group;

Y is amino, a group of the formula

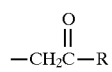

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups; a group of the formula

wherein R' is hydrogen, or a lower alkyl, lower alkynyl, or aryl group;

or a group of the formula

wherein R" is hydrogen and R'" is a lower alkyl group, optionally substituted by an aryl group, or an aryl group, said aryl group optionally substituted by one or more lower alkyl, halo, or alkoxylcarbonyl groups; or R" and R'" are both lower alkyl groups;

X is a halide, tosylate, methanesulfonate or mesitylenesulfonate ion;

and mixtures thereof, and a carrier therefor.

2. The composition of claim 1 wherein said compound has the formula wherein Y is a 2-(substituted or unsubstituted) phenyl-2-oxoethyl group.

3. The composition of claim 2 wherein said compound is 3-(2-phenyl-2-oxoethyl)-4-methylthiazolium bromide or another biologically acceptable salt thereof.

4. The composition of claim 2 wherein said compound is 3-(2-phenyl)-2-oxoethyl)thiazolium bromide or another biologically acceptable salt thereof.

5. The composition of claim 2 wherein said compound is 3-[2-(3',5'-di-tert-butyl-4'-hydroxyphenyl)-2-oxoethyl]-5-methylthiazolium bromide or another biologically acceptable salt thereof.

6. The composition of claim 2 wherein said compound is 3-[2-(3',5'-tert-butyl-4'-hydroxyphenyl)-2-oxoethyl)]-4-methyl-5-vinyl-thiazolium bromide or another biologically acceptable salt thereof.

7. The composition of claim 2 wherein said compound is 3-(2-phenyl-2-oxoethyl)-4-methyl-5-vinyl-thiazolium bromide or another biologically acceptable salt thereof.

8. The composition of claim 2 wherein said compound is 3-[2-(4'-diethylaminophenyl)-2-oxoethyl]-thiazolinium bromide or another biologically acceptable salt thereof.

9. The composition of claim 1 wherein Y is a 2-amino-2-oxoethyl group.

10. The composition of claim 8 wherein said compound is 3-(2-amino-2-oxoethyl)-benzothiazolium bromide or another biologically acceptable salt thereof.

11. The composition of claim 8 wherein said compound is 3-(2-amino-2-oxoethyl)-4-methyl-5-(2-hydroxyethyl)-thiazolium bromide or another biologically acceptable salt thereof.

12. The composition of claim 1 wherein said compound is 2,3-diaminothiazolium mesitylenesulfonate or another biologically acceptable salt thereof.

13. The composition of claim 1 wherein said compound is 3-benzyl-5-(2-hydroxyethyl)-4-methyl thiazolium chloride or another biologically acceptable salt thereof.

14. The composition of claim 1 wherein said compound is 3-amino-5-(2-hydroxyethyl)-4-methyl-thiazolium mesitylenesulfonate or another biologically acceptable salt thereof.

15. The composition of claim 1 wherein said compound is 3-(2-methyl-2-oxoethyl)thiazolium chloride or another biologically acceptable salt thereof.

16. A pharmaceutical composition for administration to an animal to inhibit the advanced glycosylation of a target protein, and reverse pre-formed advanced glycosylation crosslinks, within said animal, comprising a pharmaceutically effective amount of a compound selected from the group consisting of compounds of the formula

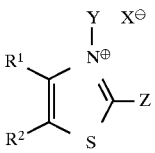

wherein $R^1$ and $R^2$ are independently selected from the group consisting of hydrogen, hydroxy(lower)alkyl, lower aceloxy(lower)alkyl, lower alkyl, lower alkenyl, or $R^1$ and $R^2$ together with their ring carbons may be an aromatic fused ring, optionally substituted by one or more amino, halo or alkylenedioxy groups;

Z is hydrogen or an amino group;

Y is amino, a group of the formula

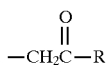

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups; a group of the formula

wherein R' is hydrogen, or a lower alkyl, lower alkynyl, or aryl group;
or a group of the formula

wherein R" is hydrogen and R'" is a lower alkyl group, optionally substituted by an aryl group, or an aryl group, said aryl group optionally substituted by one or more lower alkyl, halo, or alkoxylcarbonyl groups; or R" and R'" are both lower alkyl groups;

X is a halide, tosylate, methanesulfonate or mesitylenesulfonate ion;

and mixtures thereof, and a pharmaceutically acceptable carrier therefor.

17. The composition of claim 16 wherein said compound has the formula wherein Y is a 2-phenyl-2-oxoethyl group.

18. The composition of claim 17 wherein said compound is 3-(2-phenyl-2-oxoethyl)-4-methylthiazolium bromide or another biologically acceptable salt thereof.

19. The composition of claim 17 wherein said compound is 3-(2-phenyl-2-oxoethyl)thiazolium bromide bromide or another biologically acceptable salt thereof.

20. The composition of claim 17 wherein said compound is 3-[2-(3',5'-di-tert-butyl-4'-hydroxyphenyl)-2-oxoethyl]-5-methyl-thiazolium bromide or another biologically acceptable salt thereof.

21. The composition of claim 17 wherein said compound is 3-[2-(3',5'-tert-butyl-4'-hydroxyphenyl)-2-oxoethyl)]-4-methyl-5-vinyl-thiazolium bromide or another biologically acceptable salt thereof.

22. The composition of claim 17 wherein said compound is 3-(2-phenyl-2-oxoethyl)-4-methyl-5-vinyl-thiazolium bromide or another biologically acceptable salt thereof.

23. The composition of claim 17 wherein said compound is 3-[2-(4'-diethylaminophenyl)-2-oxoethyl]-thiazolinium bromide or another biologically acceptable salt thereof.

24. The composition of claim 16 wherein Y is a 2-amino-2-oxoethyl group.

25. The composition of claim 24 wherein said compound is 3-(2-amino-2-oxoethyl)-benzothiazolium bromide or another biologically acceptable salt thereof.

26. The composition of claim 24 wherein said compound is 3-(2-amino-2-oxoethyl)-4-methyl-5-(2-hydroxyethyl) thiazolium bromide or another biologically acceptable salt thereof.

27. The composition of claim 16 wherein said compound is 2,3-diamino-thiazolium mesitylenesulfonate or another biologically acceptable salt thereof.

28. The composition of claim 16 wherein said compound is 3-benzyl-5-(2-hydroxyethyl)-4-methylthiazolium chloride or another biologically acceptable salt thereof.

29. The composition of claim 16 wherein said compound is 3-amino-5-(2-hydroxyethyl)-4-methyl-thiazolium mesitylenesulfonate or another biologically acceptable salt thereof.

30. The composition of claim 16 wherein said compound is 3-(2-methyl-2-oxoethyl)thiazolium chloride or another biologically acceptable salt thereof.

31. A method for inhibiting the advanced glycosylation of a target protein, and reversing pre-formed advanced glycosylation crosslinks, comprising contacting the target protein with an effective amount of composition comprising a compound selected from the group consisting of compounds of the formula

wherein
R$^1$ and R$^2$ are independently selected from the group consisting of hydrogen, hydroxy(lower)alkyl, lower aceloxy(lower)alkyl, lower alkyl, lower alkenyl, or R$^1$ and R$^2$ together with their ring carbons may be an aromatic fused ring, optionally substituted by one or more amino, halo or alkylenedioxy groups;

Z is hydrogen or an amino group;

Y is amino, a group of the formula

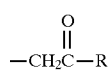

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups;
a group of the formula

wherein R' is hydrogen, or a lower alkyl, lower alkynyl, or aryl group;
or a group of the formula

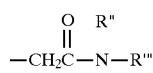

wherein R" is hydrogen and R'" is a lower alkyl group, optionally substituted by an aryl group, or an aryl group, said aryl group optionally substituted by one or more lower alkyl, halo, or alkoxylcarbonyl groups; or R" and R'" are both lower alkyl groups;

X is a halide, tosylate, methanesulfonate or mesitylenesulfonate ion;

and mixtures thereof, and a carrier therefor.

32. The method of claim 31 wherein said compound has the formula wherein Y is a 2-phenyl-2-oxoethyl group.

33. The method of claim 32 wherein said compound is 3-(2-phenyl-2-oxoethyl)-4-methylthiazolium bromide or another biologically acceptable salt thereof.

34. The method of claim 32 wherein said compound is 3-(2-phenyl-2-oxoethyl)thiazolium bromide or another biologically acceptable salt thereof.

35. The method of claim 32 wherein said compound is 3-[2-(3',5'-di-tert-butyl-4'-hydroxyphenyl)-2-oxoethyl]-5-methylthiazolium bromide or another biologically acceptable salt thereof.

36. The method of claim 32 wherein said compound is 3-[2-(3',5'-tert-butyl-4'-hydroxyphenyl)-2-oxoethyl)]-4-methyl-5-vinyl-thiazolium bromide or another biologically acceptable salt thereof.

37. The method of claim 32 wherein said compound is 3-(2-phenyl-2-oxoethyl)-4-methyl-5-vinyl-thiazolium bromide or another biologically acceptable salt thereof.

38. The method of claim 32 wherein said compound is 3-[2-(4'-diethylaminophenyl)-2-oxoethyl]-thiazolinium bromide or another biologically acceptable salt thereof.

39. The method of claim 31 wherein Y is a 2-amino-2-oxoethyl group.

40. The method of claim 39 wherein said compound is 3-(2-amino-2-oxoethyl)-benzothiazolium bromide or another biologically acceptable salt thereof.

41. The method of claim 39 wherein said compound is 3-(2-amino-2-oxoethyl)-4-methyl-5-(2-hydroxyethyl) thiazolium bromide or another biologically acceptable salt thereof.

42. The method of claim 31 wherein said compound is 2,3-diaminothiazolium mesitylenesulfonate or another biologically acceptable salt thereof.

43. The method of claim 31 wherein said compound is 3-benzyl-5-(2-hydroxyethyl)-4-methylthiazolium chloride or another biologically acceptable salt thereof.

44. The method of claim 31 wherein said compound is 3-amino-5-(2-hydroxyethyl)-4-methyl-thiazolium mesitylenesulfonate or another biologically acceptable salt thereof.

45. The method of claim 31 wherein said compound is 3-(2-methyl-2-oxoethyl)thiazolium chloride or another biologically acceptable salt thereof.

46. A method for treating an animal to inhibit the formation of advanced glycosylation endproducts, and reverse pre-formed advanced glycosylation crosslinks, of a target protein within said animal, said method comprising administering an effective amount of a pharmaceutical composition, said pharmaceutical composition comprising a compound selected from the group consisting of compounds of the formula $$\underset{R^2}{\overset{R^1}{\diagdown}} \diagup \!\!\!\! \diagdown \underset{S}{\overset{\overset{Y}{\underset{|}{N^\oplus}} \; X^\ominus}{\diagdown}} \!\!\!\! Z \qquad (I)$$

wherein $R^1$ and $R^2$ are independently selected from the group consisting of hydrogen, hydroxy(lower)alkyl, lower aceloxy(lower)alkyl, lower alkyl, lower alkenyl, or $R^1$ and $R^2$ together with their ring carbons may be an aromatic fused ring, optionally substituted by one or more amino, halo or alkylenedioxy groups;

Z is hydrogen or an amino group;

Y is amino, a group of the formula $$-CH_2\overset{\overset{O}{\|}}{C}-R$$

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups;

a group of the formula $$-CH_2R'$$

wherein R' is hydrogen, or a lower alkyl, lower alkynyl, or aryl group;

or a group of the formula $$-CH_2\overset{\overset{O}{\|}}{C}-\overset{\overset{R''}{|}}{N}-R'''$$

wherein R" is hydrogen and R'" is a lower alkyl group, optionally substituted by an aryl group, or an aryl group, said aryl group optionally substituted by one or more lower alkyl, halo, or alkoxylcarbonyl groups; or R" and R'" are both lower alkyl groups;

X is a halide, tosylate, methanesulfonate or mesitylenesulfonate ion;

and mixtures thereof, and a pharmaceutically acceptable carrier therefor.

47. The method of claim 46 wherein said compound has the formula wherein Y is a 2-phenyl-2-oxoethyl group.

48. The method of claim 47 wherein said compound is 3-(2-phenyl-2-oxoethyl)-4-methylthiazolium bromide or another biologically acceptable salt thereof.

49. The method of claim 47 wherein said compound is 3-(2-phenyl-2-oxoethyl)thiazolium bromide or another biologically acceptable salt thereof.

50. The method of claim 47 wherein said compound is 3-[2-(3',5'-di-tert-butyl-4'-hydroxyphenyl)-2-oxoethyl]-5-methylthiazolium bromide or another biologically acceptable salt thereof.

51. The method of claim 47 wherein said compound is 3-[2-(3',5'-tert-butyl-4'-hydroxyphenyl)-2-oxoethyl)]-4-methyl-5-vinyl-thiazolium bromide or another biologically acceptable salt thereof.

52. The method of claim 47 wherein said compound is 3-(2-phenyl-2-oxoethyl)-4-methyl-5-vinyl-thiazolium bromide or another biologically acceptable salt thereof.

53. The method of claim 47 wherein said compound is 3-[2-(4'-diethylaminophenyl)-2-oxoethyl]-thiazolinium bromide or another biologically acceptable salt thereof.

54. The method of claim 46 wherein Y is a 2-amino-2-oxoethyl group.

55. The method of claim 54 wherein said compound is 3-(2-amino-2-oxoethyl)-benzothiazolium bromide or another biologically acceptable salt thereof.

56. The method of claim 54 wherein said compound is 3-(2-amino-2-oxoethyl)-4-methyl-5-(2-hydroxyethyl) thiazolium bromide or another biologically acceptable salt thereof.

57. The method of claim 46 wherein said compound is 2,3-diaminothiazolium mesitylenesulfonate or another biologically acceptable salt thereof.

58. The method of claim 46 wherein said compound is 3-benzyl-5-(2-hydroxyethyl)-4-methyl thiazolium chloride or another biologically acceptable salt thereof.

59. The method of claim 46 wherein said compound is 3-amino-5-(2-hydroxyethyl)-4-methyl-thiazolium mesitylenesulfonate or another biologically acceptable salt thereof.

60. The method of claim 46 wherein said compound is 3-(2-methyl-2-oxoethyl)thiazolium chloride or another biologically acceptable salt thereof.

61. A method of inhibiting and reversing the discoloration of teeth resulting from non-enzymatic browning in the oral cavity which comprises administration of an amount effective to inhibit the formation of advanced glycosylation endproducts, and reverse pre-formed advanced glycosylation crosslinks, of a composition comprising a compound selected from the group consisting of compounds of the formula

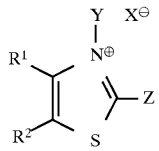 (I)

wherein $R^1$ and $R^2$ are independently selected from the group consisting of hydrogen, hydroxy(lower)alkyl, lower aceloxy(lower)alkyl, lower alkyl, lower alkenyl, or $R^1$ and $R^2$ together with their ring carbons may be an aromatic fused ring, optionally substituted by one or more amino, halo or alkylenedioxy groups;

Z is hydrogen or an amino group;

Y is amino, a group of the formula

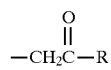

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups;

a group of the formula

wherein R' is hydrogen, or a lower alkyl, lower alkynyl, or aryl group;

or a group of the formula

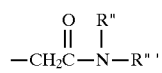

wherein R" is hydrogen and R"' is a lower alkyl group, optionally substituted by an aryl group, or an aryl group, said aryl group optionally substituted by one or more lower alkyl, halo, or alkoxylcarbonyl groups; or R" and R"' are both lower alkyl groups;

X is a halide, tosylate, methanesulfonate or mesitylenesulfonate ion;

and mixtures thereof, and a pharmaceutically acceptable carrier therefor.

62. A method of reversing advanced glycosylation endproducts formed as a consequence of the advanced glycosylation reaction by administering to a target protein a reversing amount of an agent capable of cleaving the alpha-dicarbonyl-based protein crosslinks present in the advanced glycosylation endproducts.

63. A compound of the formula

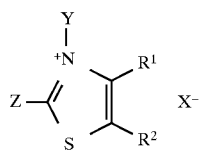 (I)

wherein Y and Z are both amino groups and $R^1$ and $R^2$ are independently selected from the group consisting of hydrogen, hydroxy(lower)alkyl, lower acyloxy(lower)alkyl, lower alkyl, lower alkenyl, or $R^1$ and $R^2$ together with their ring carbons may be an aromatic fused ring, optionally substituted by one or more amino, halo or alkylenedioxy groups; and X is a halide, tosylate, methanesulfonate or mesitylenesulfonate ion.

64. A compound of the formula

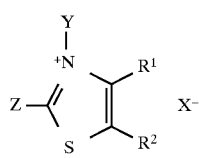 (I)

wherein $R^1$, $R^2$ and Z are hydrogen;

Y is a group of the formula

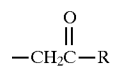

wherein R is a lower alkyl, alkoxy other than methoxy, hydroxy, amino or an aryl group, said aryl group optionally substituted by one or more lower alkyl, lower alkoxy, halo, dialkylamino, hydroxy, nitro or alkylenedioxy groups, with the proviso that Y is not 2-phenyl-2-oxoethyl or 2-(3'-methoxyphenyl)-2-oxoethyl;

a group of the formula

wherein R' is hydrogen, or a lower alkyl, lower alkynyl, or aryl group;

or a group of the formula

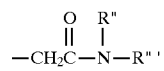

wherein R" is hydrogen and R"' is a lower alkyl group, optionally substituted by an aryl group, or an aryl group, said aryl group optionally substituted by one or more lower alkyl, halo, or alkoxylcarbonyl groups; or R" and R"' are both lower alkyl groups;

X is a halide, tosylate, methanesulfonate or mesitylenesulfonate ion.

65. A compound of the formula

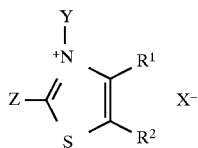 (I)

wherein R¹ and R² are independently selected from the group consisting of hydrogen, hydroxy(lower)alkyl, lower acyloxy(lower)alkyl, lower alkyl, lower alkenyl, or R¹ and R² together with their ring carbons may be an aromatic fused ring; optionally substituted by one or more amino, halo or alkylenedioxy groups;

Z is hydrogen or an amino group;

Y is amino, a group of the formula

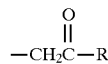

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups;

a group of the formula

wherein R' is hydrogen, a lower alkyl or aryl group; with the provisos that either Y or Z is an amino group, that when Y is amino and R² is hydrogen, then R¹ is other than hydrogen or a lower alkyl group, and when Y is amino, R¹ and R² are not methyl; and X is a halide, tosylate, methanesulfonate or mesitylenesulfonate ion.

66. The compound of claim 65 wherein Y is a 2-(substituted or unsubstituted)phenyl-2-oxoethyl group.

67. The compound 65 which is 3-[2-(3',5'-di-tert-butyl-4'-hydroxyphenyl)-2-oxoethyl]-5-methyl-thiazolium bromide or another biologically acceptable salt thereof.

68. The compound 65 which is 3-[2-(3',5'-tert-butyl-4'-hydroxyphenyl)-2-oxoethyl)]-4-methyl-5-vinyl-thiazolium bromide or another biologically acceptable salt thereof.

69. The compound 65 which is 3-(2-phenyl-2-oxoethyl)-4-methyl-5-vinyl-thiazolium bromide or another biologically acceptable salt thereof.

70. The compound 65 which is 3-[2-(4'-diethylaminophenyl)-2-oxoethyl]-thiazolinium bromide or another biologically acceptable salt thereof.

71. The compound of claim 65 wherein Y is a 2-amino-2-oxoethyl group.

72. The compound which is 3-amino-5-(2-hydroxyethyl)-4-methyl-thiazolium mesitylenesulfonate or another biologically acceptable salt thereof.

73. The compound which is 3-(2-methyl-2-oxoethyl) thiazolium chloride or another biologically acceptable salt thereof.

74. A compound 66 which is 3-(2-phenyl-2-oxoethyl)-4,5-dimethylthiazolium bromide or another biologically acceptable salt thereof.

75. A compound of claim 64 having the formula

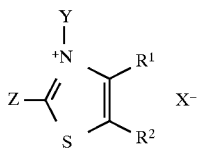 (I)

wherein

R¹, R² and Z are hydrogen;

Y is a group of the formula

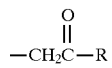

wherein R is a lower alkyl, alkoxy other than methoxy, hydroxy, amino or an aryl group, said aryl group optionally substituted by one or more lower alkyl, lower alkoxy, halo, dialkylamino, hydroxy, nitro or alkylenedioxy groups, with the proviso that Y is not 2-phenyl-2-oxoethyl or 2-(3'-methoxyphenyl)-2-oxoethyl;

X is a halide, tosylate, methanesulfonate or mesitylenesulfonate ion.

76. A compound of claim 64 having the formula

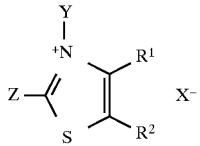 (I)

wherein

R¹, R² and Z are hydrogen;

Y is a group of the formula

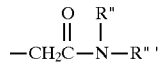

wherein R" is hydrogen and R''' is a lower alkyl group, optionally substituted by an aryl group, or an aryl group, said aryl group optionally substituted by one or more lower alkyl, halo, or alkoxylcarbonyl groups; or R" and R''' are both lower alkyl groups; and X is a halide, tosylate, methanesulfonate or mesitylenesulfonate ion.

77. A compound of claim 64 having the formula

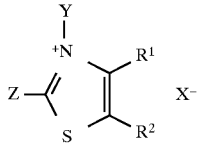 (I)

wherein R¹, R² and Z are hydrogen;

Y is a group of the formula

wherein R' is hydrogen, or a lower alkyl, lower alkynyl, or aryl group; and

X is a halide, tosylate, methanesulfonate or mesitylenesulfonate ion.

78. A compound of the formula

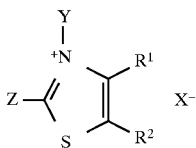 (I)

wherein $R^1$ and $R^2$ are independently selected from the group consisting of hydrogen, hydroxy(lower)alkyl, lower acyloxy(lower)alkyl, lower alkyl, lower alkenyl, or $R^1$ and $R^2$ together with their ring carbons may be an aromatic fused ring; optionally substituted by one or more amino, halo or alkylenedioxy groups;

Z is hydrogen;

Y is an alkynylmethyl group or a group of the formula

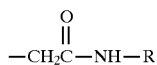

wherein R is an aryl group optionally substituted by one or more lower alkyl, halo, or alkoxylcarbonyl groups, or a lower alkyl group substituted by an aryl group, said aryl group optionally substituted by one or more lower alkyl, halo, or alkoxylcarbonyl groups; and X is a halide, tosylate, methanesulfonate or mesitylene-sulfonate ion.

79. A compound of claim 65 having the formula

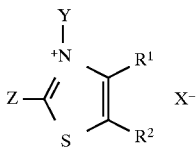 (I)

wherein $R^1$ and $R^2$ are independently selected from the group consisting of hydrogen, hydroxy(lower)alkyl, lower acyloxy(lower)alkyl, lower alkyl, lower alkenyl, or $R^1$ and $R^2$ together with their ring carbons may be an aromatic fused ring; optionally substituted by one or more amino, halo or alkylenedioxy groups;

Z is an amino group;

Y is a group of the formula

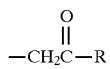

wherein R is a lower alkyl, alkoxy, hydroxy, amino or an aryl group, said aryl group optionally substituted by one or more lower alkyl, lower alkoxy, halo, dialkylamino, hydroxy, nitro or alkylenedioxy groups; and X is a halide, tosylate, methanesulfonate or mesitylene-sulfonate ion.

80. A compound of claim 68 having the formula

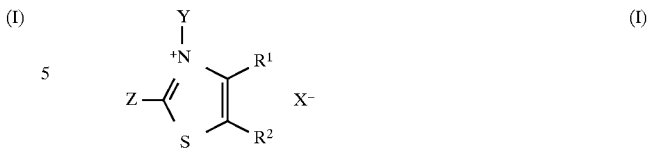 (I)

wherein $R^1$ and $R^2$ are independently selected from the group consisting of hydrogen, hydroxy(lower)alkyl, lower acyloxy(lower)alkyl, lower alkyl, lower alkenyl, or $R^1$ and $R^2$ together with their ring carbons may be an aromatic fused ring; optionally substituted by one or more amino, halo or alkylenedioxy groups;

Z is an amino group;

Y is a group of the formula

wherein R' is hydrogen, a lower alkyl or aryl group; and

X is a halide, tosylate, methanesulfonate or mesitylene-sulfonate ion.

81. A compound of claim 63 selected from the group consisting of 2,3-diamino-4-chlorobenzothiazolium mesitylenesulfonate; 2,3-diamino-4-methyl-thiazolium mesitylenesulfonate; 2,3-diamino-6-chlorobenzothiazolium mesitylenesulfonate; 2,3-diamino-5-methylthiazolium mesitylenesulfonate; 2,3-diamino-4,5-dimethyl thiazolium mesitylene sulfonate; 2,3-diamino-4-methyl-5-hydroxyethyl-thiazolium mesitylenesulfonate; 2,3-diamino-5-(3',4'-trimethylenedioxyphenyl)thiazolium mesitylene sulfonate; and another biologically acceptable salt of any one of the foregoing.

82. A compound of claim 75 selected from the group consisting of 3-(2-[4'-bromophenyl]-2-oxoethyl)-thiazolium bromide; 3-[2-(4'-methoxyphenyl)-2-oxoethyl]-thiazolium bromide; 3-[2-(2',4'-dimethoxyphenyl)-2-oxoethyl]-thiazolium bromide; 3-[2-(4'-fluorophenyl-2-oxoethyl]-thiazolium bromide; 3-[2-(2',4'-difluorophenyl)-2-oxoethyl]-thiazolium bromide; 3-[2-(4'-diethylaminophenyl)-2-oxoethyl]-thiazolium bromide; 3-(2-[1',4-benzodioxan-6-yl]-2-oxoethyl)thiazolium bromide, 3-[2-(3',4'-trimethylenedioxyphenyl)-2-oxoethyl]-thiazolium bromide; 3-[2-(3',5'-di-tert-butyl-4'-hydroxyphenyl)-2-oxoethyl]-thiazolium bromide; 3-[2-(4'-n-pentylphenyl)-2-oxoethyl]-thiazolium bromide; 3[2-(4'-chlorophenyl)-2-oxoethyl]-thiazolium bromide; 3-(2-methyl-2-oxoethyl)thiazolium chloride, and another biologically acceptable salt of any one of the foregoing.

83. A compound of clam 65 selected from the group consisting of 3-amino-4-methyl-5-[2-(2',6'-dichlorobenzyloxy)ethyl]-thioazolium mesitylenesulfonate; 3-amino-4-methyl-5-vinyl-thiazolium mesitylene sulfonate; and another biologically acceptable salt of any one of the foregoing.

84. A compound of claim 79 selected from the group consisting of 2-amino-3-(2-methoxy-2-oxoethyl)thiazolium bromide; 2-amino-3-(2-methoxy-2-oxoethyl)benzothiazolium bromide; 2-amino-3-(2-amino-2-oxoethyl)thiazolium bromide; 2-amino-3-(2-amino-2-oxoethyl)benzothiazolium bromide; and another biologically acceptable salt of any one of the foregoing.

85. The compound of claim 66 selected from the group consisting of 2,6-diamino-3[2-(4'-methoxyphenyl)-2-oxoethyl]benzothiazolium bromide; 2,6-diamino-3[2-(3'- methoxyphenyl)-2-oxoethyl]benzothiazolium bromide; 2,6-diamino-3[2-(4'-diethylaminophenyl)-2-oxoethyl]benzothiazolium bromide; 2,6-diamino-3(2-(4'-bromophenyl)-2-oxoethyl]benzothiazolium bromide; 2,6-diamino-3(2-(2-phenyl-2-oxoethyl)benzothiazolium bromide; 2,6-diamino-3[2-(4'-fluorophenyl-2-oxoethyl]benzothiazolium bromide; and another biologically acceptable salt of any one of the foregoing.

86. A compound of claim 78 selected from the group consisting of 3-[2-(2',6'-dichlorophenethylamino)-2-oxoethyl]-4-methyl-5-(2'-hydroxyethyl)-thiazolium-bromide; 3-[2-4'-carbethoxyanilino)-2-oxoethyl]-4-methyl-5-(2'-hydroxyethyl)-thiazolium bromide; 3-[2-(2',6'-diisopropylanilino)-2-oxoethyl]-4-methyl-5-(2'-hydroxyethyl)-thiazolium bromide; 3-[2-(4'-carbmethoxy-3'-hydroxyanilino)-2-oxoethyl]-4-methyl-5-(2'-hydroxyethyl)-thiazolium bromide; and another biologically acceptable salt of any one of the foregoing.

* * * * *